(12) United States Patent
Velasquez et al.

(10) Patent No.: US 11,384,357 B2
(45) Date of Patent: Jul. 12, 2022

(54) APTAMERS FOR PERSONAL CARE APPLICATIONS

(71) Applicant: The Procter & Gamble Company, Cincinnati, OH (US)

(72) Inventors: Juan Esteban Velasquez, Cincinnati, OH (US); Amy Violet Trejo, Oregonia, OH (US); Laurie Ellen Breyfogle, Milford, OH (US); James Patrick Henry, Mason, OH (US); Douglas Joseph Dobrozsi, Loveland, OH (US); Gregory Allen Penner, London (CA)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/270,937

(22) Filed: Feb. 8, 2019

(65) Prior Publication Data

US 2020/0002703 A1    Jan. 2, 2020

Related U.S. Application Data

(60) Provisional application No. 62/692,108, filed on Jun. 29, 2018.

(51) Int. Cl.
| | | |
|---|---|---|
| *C12N 15/11* | (2006.01) | |
| *C12N 15/115* | (2010.01) | |
| *A61K 8/23* | (2006.01) | |
| *A61K 8/49* | (2006.01) | |
| *A61K 8/58* | (2006.01) | |
| *A61K 8/60* | (2006.01) | |
| *A61Q 5/00* | (2006.01) | |
| *A61Q 5/02* | (2006.01) | |
| *A61Q 5/12* | (2006.01) | |
| *G01N 33/569* | (2006.01) | |

(52) U.S. Cl.
CPC .............. *C12N 15/115* (2013.01); *A61K 8/23* (2013.01); *A61K 8/4926* (2013.01); *A61K 8/4946* (2013.01); *A61K 8/58* (2013.01); *A61K 8/606* (2013.01); *A61Q 5/006* (2013.01); *A61Q 5/02* (2013.01); *A61Q 5/12* (2013.01); *G01N 33/56961* (2013.01); *C12N 2310/16* (2013.01); *C12N 2310/31* (2013.01); *C12N 2310/32* (2013.01); *C12N 2310/33* (2013.01); *C12N 2310/351* (2013.01)

(58) Field of Classification Search
CPC .. C12N 15/115; C12N 2310/16; A61Q 5/006; G01N 33/56961
See application file for complete search history.

(56) References Cited

U.S. PATENT DOCUMENTS

| | | |
|---|---|---|
| 2,946,725 A | 7/1960 | Norris |
| 3,070,510 A | 12/1962 | Cooley et al. |
| 3,429,963 A | 2/1969 | Shedlovsky |
| 3,506,720 A | 4/1970 | Model et al. |
| 3,535,421 A | 10/1970 | Briner et al. |
| 3,538,230 A | 11/1970 | Pader et al. |
| 3,678,154 A | 7/1972 | Widder et al. |
| 3,689,637 A | 9/1972 | Pader |
| 3,696,191 A | 10/1972 | Weeks |
| 3,711,604 A | 1/1973 | Colodney et al. |
| 3,737,533 A | 6/1973 | Moon et al. |
| 3,862,307 A | 1/1975 | Di Giulio |
| 3,911,104 A | 10/1975 | Harrison |
| 3,935,306 A | 1/1976 | Roberts et al. |
| 3,959,458 A | 5/1976 | Agricola et al. |
| 3,988,443 A | 10/1976 | Ploger et al. |
| 3,991,177 A | 11/1976 | Vidra et al. |
| 4,040,858 A | 8/1977 | Wason |
| 4,051,234 A | 9/1977 | Gieske et al. |
| 4,058,595 A | 11/1977 | Colodney |
| 4,138,477 A | 2/1979 | Gaffar |
| 4,154,815 A | 5/1979 | Pader |
| 4,183,914 A | 1/1980 | Gaffar |
| 4,304,766 A | 12/1981 | Chang |
| 4,355,022 A | 10/1982 | Rabussay |
| 4,590,066 A | 5/1986 | Parran, Jr. et al. |
| 4,627,977 A | 12/1986 | Gaffar et al. |
| 4,661,341 A | 4/1987 | Benedict et al. |
| 4,846,650 A | 7/1989 | Benedict et al. |
| 4,877,603 A | 10/1989 | Degenhardt et al. |
| 4,980,153 A | 12/1990 | Jackson et al. |
| 4,992,420 A | 2/1991 | Neeser |
| 5,000,939 A | 3/1991 | Dring et al. |

(Continued)

FOREIGN PATENT DOCUMENTS

| | | |
|---|---|---|
| CN | 104586362 A | 5/2015 |
| CN | 105441213 A | 3/2016 |

(Continued)

OTHER PUBLICATIONS

All final and non-final office actions for U.S. Appl. No. 16/059,396 (P&G Case 15320).
All final and non-final office actions for U.S. Appl. No. 16/059,597 (P&G Case 14919M).
All final and non-final office actions for U.S. Appl. No. 16/270,911 (P&G Case 15296).
Aristea Velegraki et al., "Malassezia Infections in Humans and Animals: Pathophysiology, Detection and Treatment", Plos Pathogens, vol. 11, No. 1, Jan. 8, 2015.

(Continued)

*Primary Examiner* — Ekaterina Poliakova-Georgantas
(74) *Attorney, Agent, or Firm* — Linda M. Sivik

(57) ABSTRACT

The present invention is directed to an aptamer composition comprising at least one oligonucleotide consisting of: deoxyribonucleotides, ribonucleotides, derivatives of deoxyribonucleotides, derivatives of ribonucleotides, and mixtures thereof; wherein said aptamer composition has a binding affinity for one or more fungi species from the genus *Malassezia*.

18 Claims, 11 Drawing Sheets

Figure 1:
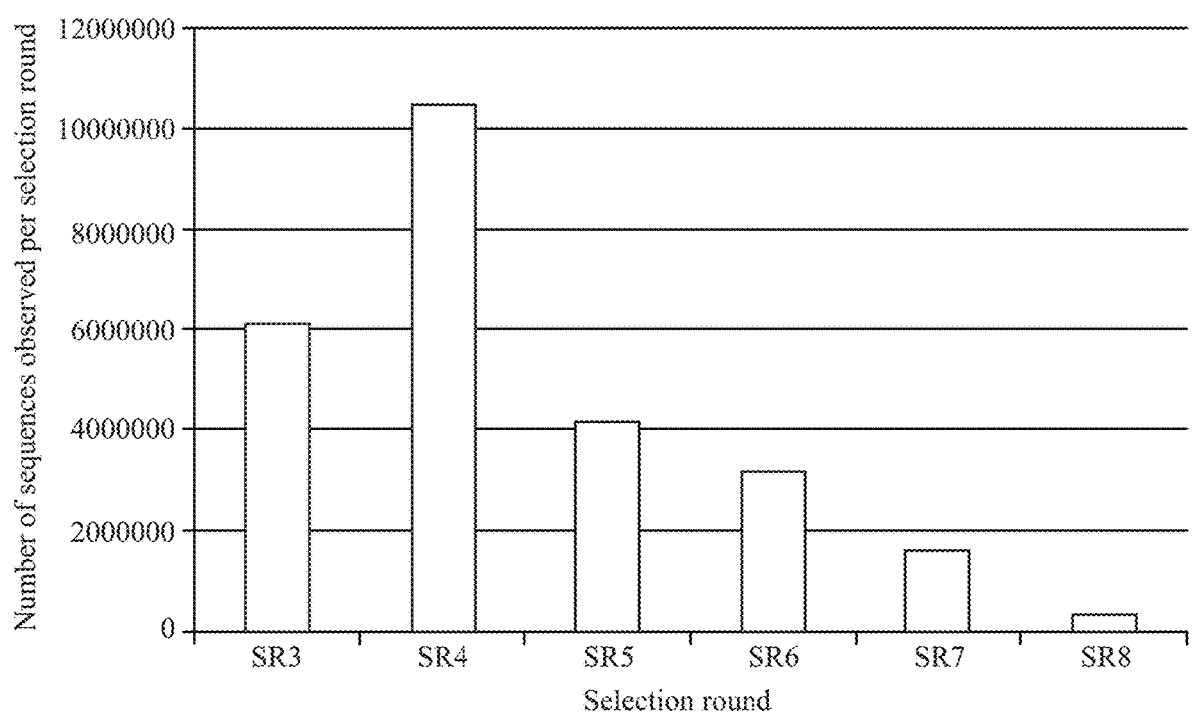

Specification includes a Sequence Listing.

(56) References Cited

U.S. PATENT DOCUMENTS

| | | |
|---|---|---|
| 5,037,637 A | 8/1991 | Gaffar et al. |
| 5,626,838 A | 5/1997 | Cavanaugh, Jr. |
| 5,827,505 A | 10/1998 | Hughes et al. |
| 5,939,052 A | 8/1999 | White, Jr. et al. |
| 6,251,372 B1 | 6/2001 | Witt et al. |
| 6,707,929 B2 | 3/2004 | Marapane |
| 7,079,158 B2 | 7/2006 | Lambertsen |
| 7,104,800 B2 | 9/2006 | Ortiz-Valero |
| 7,435,794 B2 | 10/2008 | Lukyanov |
| 7,803,922 B2 | 9/2010 | Lukyanov et al. |
| 8,119,162 B2 | 2/2012 | Miksa |
| 8,168,600 B2 | 5/2012 | Dokka |
| 8,241,651 B2 | 8/2012 | Lahann |
| 8,338,115 B2 | 12/2012 | Adler |
| 8,360,973 B2 | 1/2013 | Bazin |
| 8,484,155 B2 | 7/2013 | Yamaguchi |
| 8,871,920 B2 | 10/2014 | Purschke |
| 9,457,071 B2 | 10/2016 | Hide |
| 9,518,265 B2 | 12/2016 | Hohlig |
| 9,709,576 B2 | 7/2017 | Hide |
| 9,732,348 B2 | 8/2017 | Cauchard |
| 9,902,961 B2 | 2/2018 | Dausse |
| 9,976,145 B2 | 5/2018 | Jarosch |
| 9,996,674 B2 | 6/2018 | Segman |
| 10,001,496 B2 | 6/2018 | Jung |
| 10,231,531 B2 | 3/2019 | Witchell |
| 10,273,477 B2 | 4/2019 | Manoharan et al. |
| 10,329,575 B2 | 6/2019 | Alexandrov et al. |
| 10,650,289 B2 | 5/2020 | Szegedy |
| 10,676,396 B2 | 6/2020 | Johannsmann |
| 2002/0065452 A1 | 5/2002 | Bazin |
| 2002/0150287 A1 | 10/2002 | Kobayashi |
| 2002/0183988 A1 | 12/2002 | Skaanning |
| 2003/0014324 A1 | 1/2003 | Donovan |
| 2004/0236592 A1 | 11/2004 | Aleles |
| 2006/0085274 A1 | 4/2006 | Sottery |
| 2006/0149151 A1 | 7/2006 | Ladjevardi |
| 2006/0178904 A1 | 8/2006 | Aghassian |
| 2007/0054261 A1 | 3/2007 | Sherman |
| 2007/0058858 A1 | 3/2007 | Harville |
| 2008/0097814 A1 | 4/2008 | Koustoumbardis |
| 2008/0152600 A1 | 6/2008 | Huang et al. |
| 2010/0106679 A1 | 4/2010 | Yamaguchi |
| 2010/0254581 A1 | 10/2010 | Neeser |
| 2011/0016001 A1 | 1/2011 | Schieffelin |
| 2012/0041282 A1 | 2/2012 | Nichol |
| 2012/0190627 A1 | 7/2012 | Delattre |
| 2012/0320191 A1 | 12/2012 | Meschkat |
| 2013/0323242 A1 | 12/2013 | Everett |
| 2014/0028822 A1 | 1/2014 | Khadavi |
| 2014/0081095 A1 | 3/2014 | Krishnan |
| 2014/0216492 A1 | 8/2014 | Magri |
| 2014/0378810 A1 | 12/2014 | Davis |
| 2015/0045631 A1 | 2/2015 | Ademola |
| 2015/0217465 A1 | 8/2015 | Krenik |
| 2015/0329863 A1 | 11/2015 | Cauchard et al. |
| 2015/0353933 A1 | 12/2015 | Miyakawa et al. |
| 2016/0061602 A1 | 3/2016 | Fessi |
| 2016/0326530 A1 | 11/2016 | Dausse et al. |
| 2017/0004558 A1 | 1/2017 | Abramowitz |
| 2017/0107515 A1 | 4/2017 | Eberly et al. |
| 2017/0270593 A1 | 9/2017 | Sherman |
| 2018/0040052 A1 | 2/2018 | Robinson |
| 2018/0040053 A1 | 2/2018 | Robinson |
| 2018/0043037 A1 | 2/2018 | Dalma-weiszhausz et al. |
| 2018/0116583 A1 | 5/2018 | Cook |
| 2018/0140248 A1 | 5/2018 | Chandra |
| 2018/0223285 A1 | 8/2018 | Hohlig |
| 2018/0225673 A1 | 8/2018 | Dubey |
| 2018/0235535 A1 | 8/2018 | Cook |
| 2018/0247365 A1 | 8/2018 | Cook |
| 2018/0253866 A1 | 9/2018 | Jain |
| 2018/0349979 A1 | 12/2018 | Robinson |
| 2019/0035149 A1 | 1/2019 | Chen |
| 2019/0048348 A1 | 2/2019 | Velasquez |
| 2019/0048349 A1 | 2/2019 | Velasquez |
| 2019/0112593 A1 | 4/2019 | Penner |
| 2019/0209077 A1 | 7/2019 | Charraud |
| 2019/0350514 A1 | 11/2019 | Purwar |
| 2019/0355115 A1 | 11/2019 | Niebauer |
| 2019/0355119 A1 | 11/2019 | Hu |
| 2020/0000697 A1 | 1/2020 | Velasquez et al. |
| 2020/0002703 A1 | 1/2020 | Velasquez |
| 2020/0131515 A1 | 4/2020 | Inapuri et al. |
| 2020/0221995 A1 | 7/2020 | Mathiaszyk et al. |
| 2020/0330353 A1 | 10/2020 | Velasquez et al. |

FOREIGN PATENT DOCUMENTS

| | | | |
|---|---|---|---|
| EP | 0251591 | 7/1988 | |
| FR | 3020465 A1 | 10/2015 | |
| GB | 490384 | 8/1938 | |
| JP | 3163309 U | 9/2010 | |
| KR | 101456942 B1 | 11/2014 | |
| RU | 2306921 C1 | 9/2007 | |
| WO | 9960167 A1 | 11/1999 | |
| WO | 0191602 A2 | 12/2001 | |
| WO | 02083737 A1 | 10/2002 | |
| WO | 2006055902 A2 | 5/2006 | |
| WO | 2007149310 A2 | 12/2007 | |
| WO | WO-2010006215 A1 * | 1/2010 | ........... C12Q 1/6883 |
| WO | 2011085727 A1 | 7/2011 | |
| WO | 2015140722 A1 | 9/2015 | |
| WO | 2016176203 A1 | 11/2016 | |
| WO | WO-2017139417 A1 * | 8/2017 | ........... C12N 15/115 |
| WO | 2017207455 A1 | 12/2017 | |
| WO | 2018202065 A1 | 11/2018 | |

OTHER PUBLICATIONS

Database WPI, XP002785798, Week 201649, 2016, Thomson Scientific, London GB, AN 2016-20069A.

Gao Shunxiang et al., "Post-Selex optimization of aptamers", Analytical and Bioanalytical Chemistry, Springer, DE, vol. 108, No. 17, May 12, 2016, pp. 4567-4573.

International Search Report and Written Opinion dated Oct. 18, 2018, U.S. Appl. No. 16/059,396, 21 pgs.

International Search Report with Written opinion, dated Nov. 11, 2018, 17 pages.

Low, S.Y., et al.: "DNA aptamers bind specifically and selectively to (1-3)-beta-d-glucans", Biochemical and Biophysical Research Communications, Elsevier, Amsterdam, NL, vol. 378, No. 4, Dec. 4, 2008, pp. 701-705.

N. Shibata et al., "The cell wall galactomannan antigen from Malassezia furfur and Malassezia pachydermatis contains-1,6-linked linear galactofuranosyl residues and its detection has diagnostic potential", Journal of General Microbiology, vol. 155, No. 10, Oct. 1, 2009, pp. 3420-3429.

Nonaka Yoshihiko et al., "Screening and improvement of an anti-VEGF DNA aptamer", Molecules, vol. 15, No. 1, Jan. 7, 2010, pp. 215-225.

PCT International Search Report and Written Opinion for PCT/US2019/017151 dated Jun. 14, 2019.

PCT International Search Report and Written Opinion for PCT/US2019/017154 dated Jun. 14, 2019.

Pillaiyar Thanigaimalai et al., "Downregulation of melanogenesis: drug discovery and therapeutic options", Drug Discovery Today, Elsevier, Amsterdam, NL, vol. 22, No. 2, Sep. 28, 2016, pp. 282-298.

Tang X-L et al., "Improved detection of deeply invasive candidiasis with DNA aptamers specific binding to (1-3)-[beta]-D-glucans from Candida albicans", European Journal of Clinical Microbiology & Infectious diseases, Springer, Wiesbaden, DE, vol. 35, No. 4, Jan. 25, 2016, pp. 587-595.

Teresa Janas et al., "The selection of aptamers specific for membrane molecular targets", Cellular & Molecular Biology Letters, vol. 16, No. 1, Jun. 28, 2010, pp. 25-39.

Wei Li et al., "VEGF induces proliferation of human hair follicle dermal papilla cells through VEGFR-2-mediated activation of ERK",

(56) References Cited

OTHER PUBLICATIONS

Experimental Cell Research, Elsevier, Amsterdam, NL, vol. 318, No. 14, May 29, 2012, pp. 1633-1640.

"Jack Florek '17 presents at ACS in San Francisco", Emmanuel College, retrieved from http://gerdonlab.blogs.emmanuel.edu/2017/04/04/jack-florek-17-presents-acs-san-francisco/, Oct. 15, 2018, 6 pages.

Bawazer et al., "Efficient Selection of Biomineralizing DNA Aptamers Using Deep Sequencing and Population Clustering", ACS Nano, vol. 8, No. 1, 2014, pp. 1-10.

Eifler, Electronic Nose-Based Fusarium Detection and Deoxynivalenol Aptamer Development, Dissertation, Jul. 2014, 106 pages.

Fujii et al., "Pesticide vapor sensing using an aptamer, nanopore, and agarose gel on a chip", Lab on a Chip, vol. 17, No. 14, 2017, pp. 2421-2425.

Geron, "Introducing Capsule Networks", O'Reilly, https://www.oreilly.com/content/introducing-capsule-networks/, Feb. 6, 2018, pp. 1-7.

Hasegawa et al., "Methods for Improving Aptamer Binding Affinity", Molecules, vol. 21, No. 4, 2016, pp. 1-15.

Hurot et al., "Bio-Inspired Strategies for Improving the Selectivityand Sensitivity of Artificial Noses: A Review", Sensors, vol. 20, No. 6, 2020, pp. 1-28.

John et al., "ANYL 154: DNA aptamers that bind with high affinity to hydroxyapatite", ACS National Meeting & Exposition; 253rd National Meeting of The American-Chemical-Society (ACS) On Advanced Materials, Technologies, Systems, and Processes, American Chemical So, vol. 253, Apr. 2017, p. ANYL154.

Komarova et al., "Selection, Characterization, and Application ofssDNA Aptamer against Furaneol", Molecules, vol. 23, No. 12, 2018, pp. 1-15.

Kuznetsov et al., "Aptamer based vanillin sensor using an ion-sensitive field-effect transistor", Microchimica Acta, vol. 185, No. 1, 2017, 26 pages.

Ramos et al., "Female Pattern Hair Loss: A Clinical and Pathophysiological Review", ABD: Anais Brasileiros De Dermatologia, vol. 90, No. 4, Jul.-Aug. 2015, pp. 1-29.

Schwartz et al., "The role of oxidative damage in poor scalp health: ramifications to causality and associated hair growth", International Journal of Cosmetic Science, vol. 37, No. Suppl. 2, 2015, pp. 9-15.

\* cited by examiner

```
           (1) 1        10        20        30        40
Mg-59 (1)  CTGACGGGAGTCAGAACCCTTGTTAAGGGA CACCTGTTT
Mg-73 (1)  CTGACGGGAGTCAGAACCCTTGTTAAGGGA CACCTGTTT (1) 1        10        20        30        40
Mg-6  (1)  TCCT  TG  TGGTGAGAGG GT CAATGAATCATATTACCG
Mg-66 (1)  TCCT  TG  TGGTGAGAGGTGT CAATGAATCATATTACCG
Mg-74 (1)  TCCT  TGT TGGTGAGAGG GT CAATGAATCATATTACCG
Mg-85 (1)  TCCT  TG  TGGTGAGAGG GTT CAATGAATCATATTACCG
Mg-86 (1)  TCCTT TG  TGGTGAGAGG GT CAATGAATCATATTACCG (1) 1        10        20        30        40
Mg-20 (1)  TAAAGAA A  GAT ATCAGCAGGGTTGATTTTGAT GATG
Mg-4  (1)  TAAAGAA A  GAT ATCAGCAGGGTTGATTTTGA  GATG
Mg-43 (1)  TAAAGAA AA GAT ATCAGCAGGGTTGATTTTGA  GATG
Mg-58 (1)  TAAAGAA AA GATA ATCAGCAGGGTTGATTTTGA GATG
Mg-64 (1)  TAAAGAAT A  GAT ATCAGCAGGGTTGATTTTGA GATG
```

Figure 9

|          | (1) | 1          10         20         30         40 |
|----------|-----|---------------------------------------------------|
| Mg-20 | (1) | CACGAAACATAA TT TGTCAGAATA A  T TTTC TCT |
| Mg-4  | (1) | CACGAAACATAA TT TGTCAGAATA A  T TTTC  CT |
| Mg-43 | (1) | CACGAAACATAA TT TGTCAGAATA A  TA TTC  CT |
| Mg-58 | (1) | CACGAAACATAA TT TGTCAGAATAT A  T TTTC  CT |
| Mg-64 | (1) | CACGAAACATAA TT TGTCAGAATA A  T TTTC  CTA |
| Mg-65 | (1) | CACGAAACATAA TTA TGTCAGAATA A  T TTTC  CT |
| Mg-71 | (1) | CACGAAACATAA TT TGTCAGAATA A  TT TTTC  TT |
| Mg-72 | (1) | CACGAAACATAAA TT TGTCAGAATA A  T TTTC  CT |
| Mg-80 | (1) | CACGAAACATAA TT TGTCAGAATA AT T TTTC  CT |

Figure 10

Figure 11

SEQUENCE LISTING

```
<160> NUMBER OF SEQ ID NOS: 103

<210> SEQ ID NO 1
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 1
tagggaagag aaggacatat gatttgagac ggtatgaagg cttttgagaa aatgcgccac      60
gaattgacta gtacatgacc acttga                                          86

<210> SEQ ID NO 2
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 2
tagggaagag aaggacatat gattggcaag tatttgtaca tatactgacg tttgccttac      60
```

```
tgcttgacta gtacatgacc acttga                                          86
```

<210> SEQ ID NO 3
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 3

```
tagggaagag aaggacatat gatgaccgag gttccggcga cagagcaaat ttgtaatttg    60
gagttgacta gtacatgacc acttga                                          86
```

<210> SEQ ID NO 4
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 4

```
tagggaagag aaggacatat gatcacgaaa cataagttgt gtcagaatac acctgtttcc    60
ctgttgacta gtacatgacc acttga                                          86
```

<210> SEQ ID NO 5
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 5

```
tagggaagag aaggacatat gattaaagaa caggatgatc agggttgatg gattttgacg    60
atgttgacta gtacatgacc acttga                                          86
```

<210> SEQ ID NO 6
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 6

```
tagggaagag aaggacatat gattcctctg ctggtgagag gcgtccaatg aatcatatta    60
ccgttgacta gtacatgacc acttga                                          86
```

<210> SEQ ID NO 7
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 7

```
tagggaagag aaggacatat gatagtcaaa taaaattttg tgtgaatcga gtgtgctatt    60
gctttgacta gtacatgacc acttga                                          86
```

<210> SEQ ID NO 8
<211> LENGTH: 86
<212> TYPE: DNA
<213> ORGANISM: Artificial Sequence
<220> FEATURE:

<223> OTHER INFORMATION: Synthetic Aptamer Sequence

<400> SEQUENCE: 8
tagggaagag aaggacatat gatggtgttg aaagttatgt aattatttag ggaacgtatg    60
gacttgacta gtacatgacc acttga    86

<210> SEQ ID NO 9
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 9
tagggaagag aaggacatat gatggggaag agtgataatc taaaggtact acaatgtact    60
acattgacta gtacatgacc acttga    86

<210> SEQ ID NO 10
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 10
tagggaagag aaggacatat gattagcaag tatttgtaca tatactgacg tttgccttac    60
tgcttgacta gtacatgacc acttga    86

<210> SEQ ID NO 11
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 11
tagggaagag aaggacatat gatacccctcg atacgtatat tcgatatgag ggagtattcc    60
gtgttgacta gtacatgacc acttga    86

<210> SEQ ID NO 12
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 12
tagggaagag aaggacatat gatgagtaac agttcaacct tgttattaca ctaactccgt    60
gacttgacta gtacatgacc acttga    86

<210> SEQ ID NO 13
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 13
tagggaagag aaggacatat gatgatgttg ataaatttgc aatgactaga tccatccgct    60
ttattgacta gtacatgacc acttga    86

<210> SEQ ID NO 14
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 14
tagggaagag aaggacatat gatgaacgga tccgatacga acgttaacaa atgagggttt    60
aagttgacta gtacatgacc acttga                                        86

<210> SEQ ID NO 15
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 15
tagggaagag aaggacatat gataattgat atgcagcaat taccagtata aggcatctac    60
tacttgacta gtacatgacc acttga                                        86

<210> SEQ ID NO 16
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 16
tagggaagag aaggacatat gatccatttt ctcgactttg ccattgctat aaatagcttc    60
acattgacta gtacatgacc acttga                                        86

<210> SEQ ID NO 17
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 17
tagggaagag aaggacatat gattggcaaa tatttgtaca tatactgacg tttgccttac    60
tgcttgacta gtacatgacc acttga                                        86

<210> SEQ ID NO 18
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 18
tagggaagag aaggacatat gatatattca cgctagtggg agcgctgttg atcatacggc    60
tgcttgacta gtacatgacc acttga                                        86

<210> SEQ ID NO 19
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 19

```
tagggaagag aaggacatat gattggcaag tatttgtaca tatactgacg tttgtcttac    60
tgcttgacta gtacatgacc acttga                                        86

<210> SEQ ID NO 20
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 20
tagggaagag aaggacatat gatcacgaaa cataagttgt gtcagaatac acctgtttct    60
ctgttgacta gtacatgacc acttga                                        86

<210> SEQ ID NO 21
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 21
tagggaagag aaggacatat gatattaagt taggtccgta atgacactta aacggatcca    60
tacttgacta gtacatgacc acttga                                        86

<210> SEQ ID NO 22
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 22
tagggaagag aaggacatat gattggcaag tatttgtaca tatactgacg tttgccttac    60
tacttgacta gtacatgacc acttga                                        86

<210> SEQ ID NO 23
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 23
tagggaagag aaggacatat gattaaagaa caggatgatc agggttgatg gattttgatg    60
atgttgacta gtacatgacc acttga                                        86

<210> SEQ ID NO 24
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 24
tagggaagag aaggacatat gattaggcta actgttcagg gatttgatat gcatgaggag    60
cacttgacta gtacatgacc acttga                                        86

<210> SEQ ID NO 25
<211> LENGTH: 86
<212> TYPE: DNA
<213> ORGANISM: Artificial Sequence
```

```
<220> FEATURE:
<223> OTHER INFORMATION: Synthetic Aptamer Sequence

<400> SEQUENCE: 25
tagggaagag aaggacatat gattggcaag tatttgtaca tatactaacg tttgccttac    60
tgcttgacta gtacatgacc acttga                                        86

<210> SEQ ID NO 26
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 26
tagggaagag aaggacatat gattgacaag tatttgtaca tatactgacg tttgccttac    60
tgcttgacta gtacatgacc acttga                                        86

<210> SEQ ID NO 27
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 27
tagggaagag aaggacatat gattctcgag tgcaaaaacg ttgagccaag aatttaacct    60
atcttgacta gtacatgacc acttga                                        86

<210> SEQ ID NO 28
<211> LENGTH: 86
<212> TYPE: DNA
<213> ORGANISM: Artificial Sequence
<220> FEATURE:
<223> OTHER INFORMATION: Synthetic Aptamer Sequencee

<400> SEQUENCE: 28
tagggaagag aaggacatat gattggcaag tatttgtaca tatactgacg tttgccttac    60
tgtttgacta gtacatgacc acttga                                        86

<210> SEQ ID NO 29
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 29
tagggaagag aaggacatat gattggcaag tatttgtaca tatactgatg tttgccttac    60
tgcttgacta gtacatgacc acttga                                        86

<210> SEQ ID NO 30
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 30
tagggaagag aaggacatat gattggcaag tatttgtaca tatactgacg tttgccttat    60
tgcttgacta gtacatgacc acttga                                        86
```

```
<210> SEQ ID NO 31
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 31
tagggaagag aaggacatat gattggtaag tatttgtaca tatactgacg tttgccttac    60
tgcttgacta gtacatgacc acttga                                        86

<210> SEQ ID NO 32
<211> LENGTH: 86
<212> TYPE: DNA
<213> ORGANISM: Artificial Sequence
<220> FEATURE:
<223> OTHER INFORMATION: Synthetic Aptamer Sequencee

<400> SEQUENCE: 32
tagggaagag aaggacatat gatgtcaatc tatcacaaac gcgaggtaag gcccacgcga    60
ttattgacta gtacatgacc acttga                                        86

<210> SEQ ID NO 33
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 33
tagggaagag aaggacatat gatcgctcta attggcgtgg agggagtgtt cctccaacgg    60
taattgacta gtacatgacc acttga                                        86

<210> SEQ ID NO 34
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 34
tagggaagag aaggacatat gatgcatgca cgtctgaaga aatccttgaa ttgtaccgga    60
agattgacta gtacatgacc acttga                                        86

<210> SEQ ID NO 35
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 35
tagggaagag aaggacatat gattggcaag tatttgtaca tatactgacg tttaccttac    60
tgcttgacta gtacatgacc acttga                                        86

<210> SEQ ID NO 36
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 36
```
tagggaagag aaggacatat gatctaaaca gtacttcaac ctaaagagtc acgtacgcag    60
taattgacta gtacatgacc acttga                                        86

<210> SEQ ID NO 37
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 37
tagggaagag aaggacatat gattgccatc gtataaatct caaaagggat cattgtaaaa    60
tccttgacta gtacatgacc acttga                                        86

<210> SEQ ID NO 38
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 38
tagggaagag aaggacatat gatctggggg cttcccggag ttccgtaaag tagtgagatc    60
ttgttgacta gtacatgacc acttga                                        86

<210> SEQ ID NO 39
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 39
tagggaagag aaggacatat gatttgtgat caagaaaatg gaacccacat aactattccg    60
agtttgacta gtacatgacc acttga                                        86

<210> SEQ ID NO 40
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 40
tagggaagag aaggacatat gatgagccta gatcattttg atcttgcaat ctatggcaga    60
atcttgacta gtacatgacc acttga                                        86

<210> SEQ ID NO 41
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 41
tagggaagag aaggacatat gatacaattt ggatagtacc gcgatcaggt acaaagaata    60
ttcttgacta gtacatgacc acttga                                        86

<210> SEQ ID NO 42
<211> LENGTH: 86
<212> TYPE: DNA

```
<213> ORGANISM: Artificial Sequence
<220> FEATURE:
<223> OTHER INFORMATION: Synthetic Aptamer Sequence

<400> SEQUENCE: 42
tagggaagag aaggacatat gatgcattca cagtagcaat tgtatttcct tgataggaat      60
gaattgacta gtacatgacc acttga                                          86

<210> SEQ ID NO 43
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 43
tagggaagag aaggacatat gatcacgaaa cataagttgt gtcagaatac acctatttcc      60
ctgttgacta gtacatgacc acttga                                          86

<210> SEQ ID NO 44
<211> LENGTH: 86
<212> TYPE: DNA
<213> ORGANISM: Artificial Sequence
<220> FEATURE:
<223> OTHER INFORMATION: Synthetic Aptamer Sequencee

<400> SEQUENCE: 44
tagggaagag aaggacatat gattggcaag tatttgtaca tatattgacg tttgccttac      60
tgcttgacta gtacatgacc acttga                                          86

<210> SEQ ID NO 45
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 45
tagggaagag aaggacatat gattgtggaa accaaataga agatataaca ctcttatcta      60
cagttgacta gtacatgacc acttga                                          86

<210> SEQ ID NO 46
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 46
tagggaagag aaggacatat gattgaagtg gagaccgtag aggagattac aatatgaatc      60
cggttgacta gtacatgacc acttga                                          86

<210> SEQ ID NO 47
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 47
tagggaagag aaggacatat gattggcaag tatttgtaca tatactgaca tttgccttac      60
tgcttgacta gtacatgacc acttga                                          86
```

<210> SEQ ID NO 48
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 48
tagggaagag aaggacatat gatctcagta ctgcaaggat ttaagataca gcgcattgca    60
gaattgacta gtacatgacc acttga                                        86

<210> SEQ ID NO 49
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 49
tagggaagag aaggacatat gattggcaag tatttataca tatactgacg tttgccttac    60
tgcttgacta gtacatgacc acttga                                        86

<210> SEQ ID NO 50
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 50
tagggaagag aaggacatat gatttaaaca ggatccgcac gaatacagtg tacacaattc    60
aggttgacta gtacatgacc acttga                                        86

<210> SEQ ID NO 51
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 51
tagggaagag aaggacatat gatctatgga tcgactagta atcaagcctt cggactctta    60
tgattgacta gtacatgacc acttga                                        86

<210> SEQ ID NO 52
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 52
tagggaagag aaggacatat gattggggac gtaacagtat gaacttgaag acttatcatt    60
gtattgacta gtacatgacc acttga                                        86

<210> SEQ ID NO 53
<211> LENGTH: 86
<212> TYPE: DNA
<213> ORGANISM: Artificial Sequence
<220> FEATURE:
<223> OTHER INFORMATION: Synthetic Aptamer Sequence -continued

<400> SEQUENCE: 53
tagggaagag aaggacatat gattggcaag tatttgtata tatactgacg tttgccttac    60
tgcttgacta gtacatgacc acttga                                         86

<210> SEQ ID NO 54
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 54
tagggaagag aaggacatat gattggcaag tatttgtaca tatactgacg tttgctttac    60
tgcttgacta gtacatgacc acttga                                         86

<210> SEQ ID NO 55
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 55
tagggaagag aaggacatat gatcaggaat gcttcaattc cttgtagcat tcacttgtag    60
acattgacta gtacatgacc acttga                                         86

<210> SEQ ID NO 56
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 56
tagggaagag aaggacatat gattacgggg ataaggagca acatattaag caaagtacta    60
aaattgacta gtacatgacc acttga                                         86

<210> SEQ ID NO 57
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 57
tagggaagag aaggacatat gataaaacat gaagctgaac gcgtaactcc cggctggcga    60
atattgacta gtacatgacc acttga                                         86

<210> SEQ ID NO 58
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 58
tagggaagag aaggacatat gatcacgaaa cataagttgt gtcagaatat acctgtttcc    60
ctgttgacta gtacatgacc acttga                                         86

<210> SEQ ID NO 59
<211> LENGTH: 86

```
<212> TYPE: DNA
<213> ORGANISM: Artificial Sequence
<220> FEATURE:
<223> OTHER INFORMATION: Synthetic Aptamer Sequence

<400> SEQUENCE: 59
tagggaagag aaggacatat gatctgacgg gagtcagaac ccttgttaag ggaccacctg    60
tttttgacta gtacatgacc acttga                                        86

<210> SEQ ID NO 60
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 60
tagggaagag aaggacatat gatgtaagac ttgtactatg aaatgttatg gaggatgtag    60
attttgacta gtacatgacc acttga                                        86

<210> SEQ ID NO 61
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 61
tagggaagag aaggacatat gatgccgtaa gaaacctcct ggtgttcgaa atatggaaag    60
tctttgacta gtacatgacc acttga                                        86

<210> SEQ ID NO 62
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 62
tagggaagag aaggacatat gatgagtttt aaaaggcaat atgtcttgag agacaaggtt    60
agattgacta gtacatgacc acttga                                        86

<210> SEQ ID NO 63
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 63
tagggaagag aaggacatat gatattgaca ttctaagcta atgaaagtgt aataacgact    60
agcttgacta gtacatgacc acttga                                        86

<210> SEQ ID NO 64
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 64
tagggaagag aaggacatat gatcacgaaa cataagttgt gtcagaatac acctgtttcc    60
```
ctattgacta gtacatgacc acttga 86

<210> SEQ ID NO 65
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 65
tagggaagag aaggacatat gatcacgaaa cataagttat gtcagaatac acctgtttcc    60
ctgttgacta gtacatgacc acttga    86

<210> SEQ ID NO 66
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 66
tagggaagag aaggacatat gattcctctg ctggtgagag gtgtccaatg aatcatatta    60
ccgttgacta gtacatgacc acttga    86

<210> SEQ ID NO 67
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 67
tagggaagag aaggacatat gatagagtaa gaatccataa tttggcaagt agacattcgc    60
atattgacta gtacatgacc acttga    86

<210> SEQ ID NO 68
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 68
tagggaagag aaggacatat gatgtttagg acgtatctta gagctggccc tcaatgaaag    60
gttttgacta gtacatgacc acttga    86

<210> SEQ ID NO 69
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 69
tagggaagag aaggacatat gatgagaggc agtaggtcta atgaagaatc tctaggttgc    60
aaattgacta gtacatgacc acttga    86

<210> SEQ ID NO 70
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 70
tagggaagag aaggacatat gatggcctat acttggttgc ttctatagct tagtgcgggg    60
gatttgacta gtacatgacc acttga    86

<210> SEQ ID NO 71
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 71
tagggaagag aaggacatat gatcacgaaa cataagttgt gtcagaatac acttgtttcc    60
ctgttgacta gtacatgacc acttga    86

<210> SEQ ID NO 72
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 72
tagggaagag aaggacatat gatcacgaaa cataaattgt gtcagaatac acctgtttcc    60
ctgttgacta gtacatgacc acttga    86

<210> SEQ ID NO 73
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 73
tagggaagag aaggacatat gatctgacgg gagtcagaac ccttgttaag ggatcacctg    60
tttttgacta gtacatgacc acttga    86

<210> SEQ ID NO 74
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 74
tagggaagag aaggacatat gattcctctg ttggtgagag gcgtccaatg aatcatatta    60
ccgttgacta gtacatgacc acttga    86

<210> SEQ ID NO 75
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 75
tagggaagag aaggacatat gatcacaacg taattttcgg gtgaatgatg cagccaagag    60
aaattgacta gtacatgacc acttga    86

<210> SEQ ID NO 76

```
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 76
tagggaagag aaggacatat gattaagttg gaaagtggta gaatgcttag acaggcgggg    60
gacttgacta gtacatgacc acttga                                        86

<210> SEQ ID NO 77
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 77
tagggaagag aaggacatat gatgttataa tggtgcaaac tatagctaat aagatgccac    60
tgattgacta gtacatgacc acttga                                        86

<210> SEQ ID NO 78
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 78
tagggaagag aaggacatat gatgtgaatt cgcatgactt ggaagaggta aacaaaagta    60
gctttgacta gtacatgacc acttga                                        86

<210> SEQ ID NO 79
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 79
tagggaagag aaggacatat gataaggttt actcaactcg gattcaaaga acatgtactt    60
aacttgacta gtacatgacc acttga                                        86

<210> SEQ ID NO 80
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 80
tagggaagag aaggacatat gatcacgaaa cataagttgt gtcagaatac atctgtttcc    60
ctgttgacta gtacatgacc acttga                                        86

<210> SEQ ID NO 81
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 81
tagggaagag aaggacatat gatgctcgtt tattcggacc tcagggctg tcagcatttg     60
```
aatttgacta gtacatgacc acttga                                          86

<210> SEQ ID NO 82
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 82
tagggaagag aaggacatat gattgcggct ataagtttat gtgtgaatat tggtatgata    60
taattgacta gtacatgacc acttga                                          86

<210> SEQ ID NO 83
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 83
tagggaagag aaggacatat gatgacgcac agtatgcgtg ctatcaattt tgagtatagt    60
gtattgacta gtacatgacc acttga                                          86

<210> SEQ ID NO 84
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 84
tagggaagag aaggacatat gattggcaag tatttgtaca tatactgacg cttgccttac    60
tgcttgacta gtacatgacc acttga                                          86

<210> SEQ ID NO 85
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 85
tagggaagag aaggacatat gattcctctg ctggtgagag gcgttcaatg aatcatatta    60
ccgttgacta gtacatgacc acttga                                          86

<210> SEQ ID NO 86
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 86
tagggaagag aaggacatat gattcctttg ctggtgagag gcgtccaatg aatcatatta    60
ccgttgacta gtacatgacc acttga                                          86

<210> SEQ ID NO 87
<211> LENGTH: 86
<212> TYPE: DNA
<213> ORGANISM: Artificial Sequence
<220> FEATURE:

<223> OTHER INFORMATION: Synthetic Aptamer Sequence

<400> SEQUENCE: 87
tagggaagag aaggacatat gatctgacac cattttacaa attgaaataa tacagcttat    60
acgttgacta gtacatgacc acttga    86

<210> SEQ ID NO 88
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 88
tagggaagag aaggacatat gatccgcctg acgaacacaa ggaaccggaa ttaagcgaat    60
gccttgacta gtacatgacc acttga    86

<210> SEQ ID NO 89
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 89
tagggaagag aaggacatat gattgactag tacatgacca cttgagatcg gaagagcaca    60
cgtttgacta gtacatgacc acttga    86

<210> SEQ ID NO 90
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 90
tagggaagag aaggacatat gatcttatac caatcaataa cgcgcatttt tagcaagaca    60
agattgacta gtacatgacc acttga    86

<210> SEQ ID NO 91
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 91
tagggaagag aaggacatat gattaaagaa caagatgatc agggttgatg gattttgacg    60
atgttgacta gtacatgacc acttga    86

<210> SEQ ID NO 92
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 92
tagggaagag aaggacatat gattaaagaa taggatgatc agggttgatg gattttgacg    60
atgttgacta gtacatgacc acttga    86

```
<210> SEQ ID NO 93
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 93
tagggaagag aaggacatat gattcgcaga attctaatag acctggagaa gacaggggt      60 tatttgacta gtacatgacc acttga                                          86

<210> SEQ ID NO 94
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 94
tagggaagag aaggacatat gatattacga gtttataaga tttggcgctg cctactcatc     60
atcttgacta gtacatgacc acttga                                          86

<210> SEQ ID NO 95
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 95
tagggaagag aaggacatat gattaaagaa caagataatc agggttgatg gattttgacg     60
atgttgacta gtacatgacc acttga                                          86

<210> SEQ ID NO 96
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 96
tagggaagag aaggacatat gatacataaa atttccagat ctacctgatg tgtgccgtct     60
atattgacta gtacatgacc acttga                                          86

<210> SEQ ID NO 97
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 97
tagggaagag aaggacatat gatcggatga ataaacaatg ctgggtactg atcagtatga     60
cctttgacta gtacatgacc acttga                                          86

<210> SEQ ID NO 98
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 98
```
tagggaagag aaggacatat gatgaagggc aagccttata aattcgtact gtatcttatt    60
gaattgacta gtacatgacc acttga                                        86

<210> SEQ ID NO 99
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 99
tagggaagag aaggacatat gatcggtgtc ggtagaaaca aagagaggtt atgcatatct    60
atgttgacta gtacatgacc acttga                                        86

<210> SEQ ID NO 100
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 100
tagggaagag aaggacatat gatcaaggat gtcatggaac tggtgaactg tctaaaatca    60
ccattgacta gtacatgacc acttga                                        86

<210> SEQ ID NO 101
<211> LENGTH: 10
<212> TYPE: DNA
<213> ORGANISM: Artificial Sequence
<220> FEATURE:
<223> OTHER INFORMATION: Synthetic Aptamer Sequence
<220> FEATURE:
<221> NAME/KEY: misc_feature
<222> LOCATION: (10)..(10)
<223> OTHER INFORMATION: n is a, c, g, or t

<400> SEQUENCE: 101 ggtatgaagn                                                          10

<210> SEQ ID NO 102
<211> LENGTH: 10
<212> TYPE: DNA
<213> ORGANISM: Artificial Sequence
<220> FEATURE:
<223> OTHER INFORMATION: Synthetic Aptamer Sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 102 nnaaaatgnn                                                          10

<210> SEQ ID NO 103
<211> LENGTH: 25
<212> TYPE: DNA
<213> ORGANISM: Artificial Sequence
<220> FEATURE:
<223> OTHER INFORMATION: Synthetic Aptamer Sequence
<220> FEATURE:
<221> NAME/KEY: misc_feature
<222> LOCATION: (10)..(16)
<223> OTHER INFORMATION: n is a, c, g, or t

```
<220> FEATURE:
<221> NAME/KEY: misc_feature
<222> LOCATION: (18)..(19)
<223> OTHER INFORMATION: n is a, c, g, or t

<400> SEQUENCE: 103
ggtatgaagn nnnnnnanna aaatg                                          25
```

APTAMERS FOR PERSONAL CARE APPLICATIONS

FIELD OF INVENTION

The present invention generally relates to nucleic acid aptamers that have a high binding affinity and specificity for fungi of the genus *Malassezia*. This invention also relates to the use of such aptamers as delivery vehicles of active ingredients to the scalp and the skin.

BACKGROUND OF THE INVENTION

Aptamers are short single-stranded oligonucleotides, with a specific and complex three-dimensional shape, that bind to target molecules. The molecular recognition of aptamers is based on structure compatibility and intermolecular interactions, including electrostatic forces, van der Waals interactions, hydrogen bonding, and π-π stacking interactions of aromatic rings with the target material. The targets of aptamers include, but are not limited to, peptides, proteins, nucleotides, amino acids, antibiotics, low molecular weight organic or inorganic compounds, and even whole cells. The dissociation constant of the complexes of aptamers and the corresponding target materials typically varies between micromolar and picomolar levels, which is comparable to the affinity of antibodies to their antigens. Aptamers can also be designed to have high specificity, enabling the discrimination of target molecules from closely related derivatives.

Aptamers are usually designed in vitro from large libraries of random nucleic acids by Systematic Evolution of Ligands by Exponential Enrichment (SELEX). The SELEX method was first introduced in 1990 when single stranded RNAs are selected against low molecular weight dyes (Ellington, A. D., Szostak, J. W., 1990. Nature 346: 818-822). A few years later, single stranded DNA aptamers and aptamers containing chemically modified nucleotides are also described (Ellington, A. D., Szostak, J. W., 1992. Nature 355: 850-852; Green, L. S., et al., 1995. Chem. Biol. 2: 683-695). Since then, aptamers for hundreds of microscopic targets, such as cations, small molecules, proteins, cells, or tissues have been selected. A compilation of examples from the literature is included in the database at the website: http://www.aptagen.com/aptamer-index/aptamer-list.aspx. However, a need still exists for aptamers that selectively bind to fungi of the genus *Malassezia*, including *M. globosa*. These aptamers could be used to effectively deliver active ingredients, such as anti-fungal agents, to the scalp or the skin.

SUMMARY OF THE INVENTION

In this invention, we have demonstrated the use of SELEX for the selection of aptamers against strains of the genus *Malassezia* and the use of such aptamers for the delivery of active ingredients to the scalp or the skin.

In the present invention, an aptamer composition is provided. The aptamer composition may comprise at least one oligonucleotide consisting of deoxyribonucleotides, ribonucleotides, derivatives of deoxyribonucleotides, derivatives of ribonucleotides, and mixtures thereof, wherein said aptamer composition has a binding affinity for one or more fungi species from the genus *Malassezia*.

In the present invention, an aptamer composition is provided. The aptamer composition may comprise at least one oligonucleotide selected from the group consisting of SEQ ID NO 1, SEQ ID NO 2, and SEQ ID NO 4.

In the present invention, the aptamer composition may comprises at least one oligonucleotide comprising one or more motifs selected from the group consisting of SEQ ID NO 101, SEQ ID NO 102, and SEQ ID NO 103.

In the present invention, a personal care composition is provided. The personal care composition may comprise at least one nucleic acid aptamer, wherein said at least one nucleic acid aptamer has a binding affinity for one or more fungi species from the genus *Malassezia*.

In the present invention, a method for delivering one or more personal care active ingredients to the scalp or the skin is provided. The method may comprise administering a personal care composition comprising at least one nucleic acid aptamer and one or more personal care active ingredients, wherein said at least one nucleic acid aptamer and said one or more personal care active ingredients are covalently or non-covalently attached, and wherein said at least one nucleic acid aptamer has a binding affinity for one or more fungi species from the genus *Malassezia*.

In the present invention, a method for delivering one or more personal care active ingredients to the scalp of the skin is provided. The method may comprise administering a personal care composition comprising at least one nucleic acid aptamer and one or more nanomaterials, wherein said at least one nucleic acid aptamer and said one or more nanomaterials are covalently or non-covalently attached, wherein said at least one nucleic acid aptamer has a binding affinity for one or more fungi species from the genus *Malassezia*, and wherein said one or more nanomaterials comprise one or more personal care active ingredients.

BRIEF DESCRIPTION OF THE DRAWING FIGURES

For a more complete understanding of the disclosure, reference should be made to the following detailed description and drawing Figures.

FIG. 1. Total number of sequences on each selection round.

Figure 2:
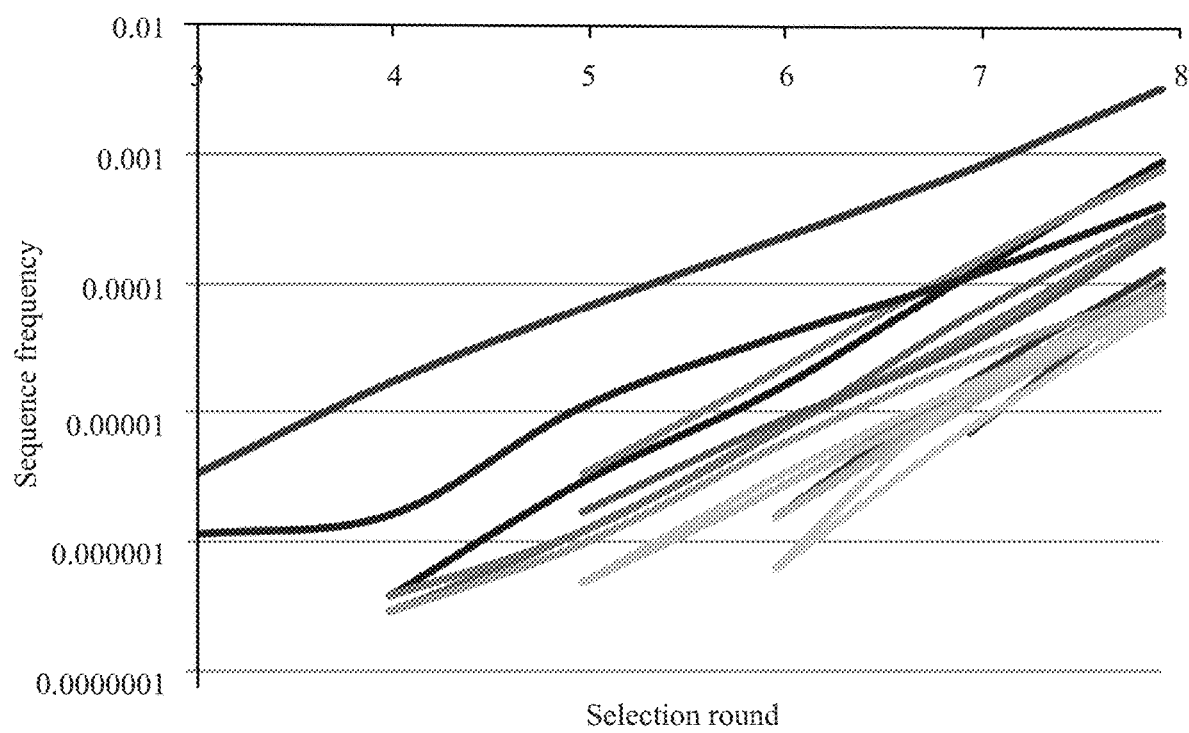

FIG. 2. The enrichment trajectories of the top twenty sequences in terms of copy number across different selection rounds.

Figure 3:
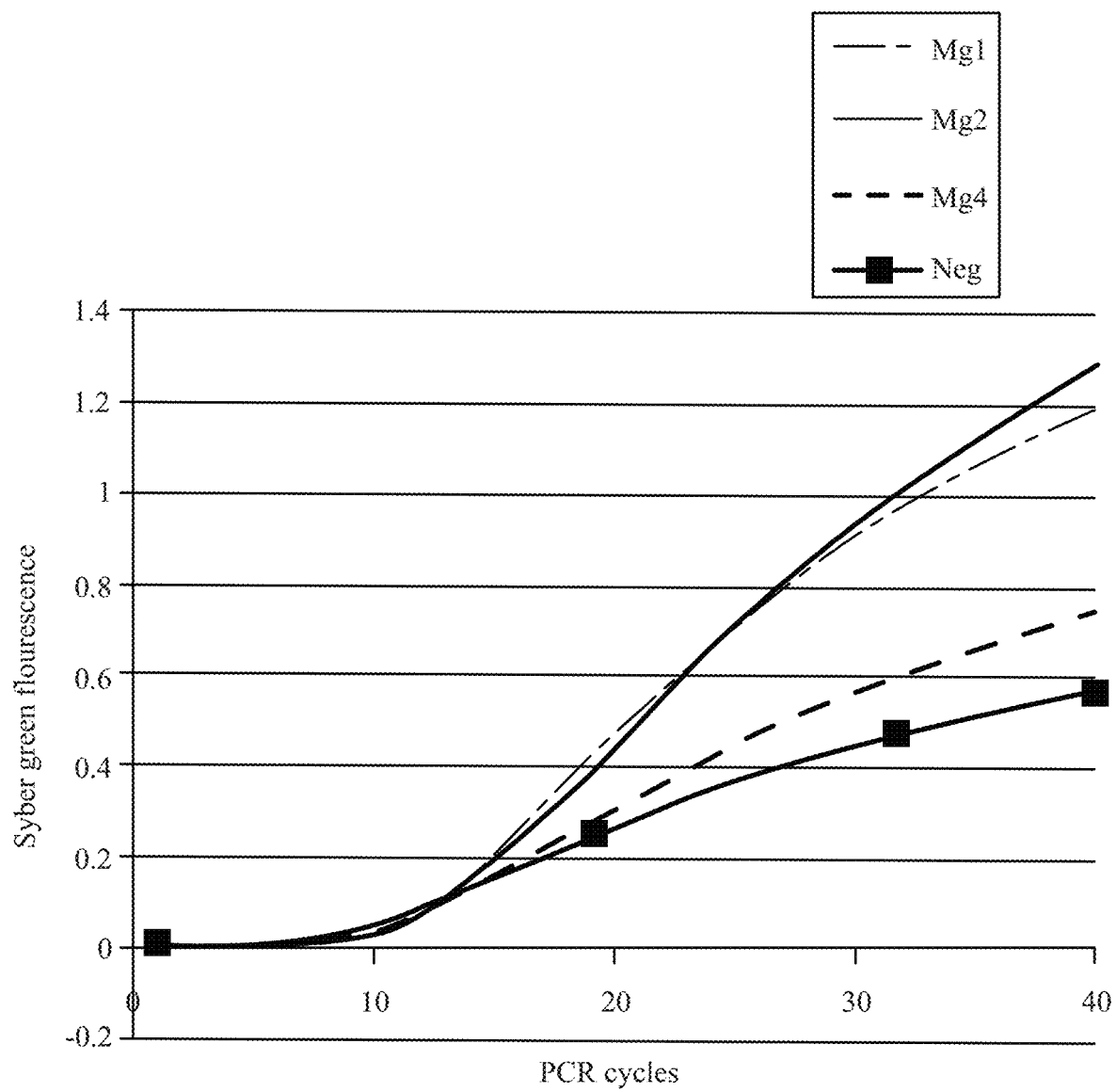

FIG. 3. Binding of different aptamers to *M. globosa* as demonstrated by qPCR analysis.

Figure 4:
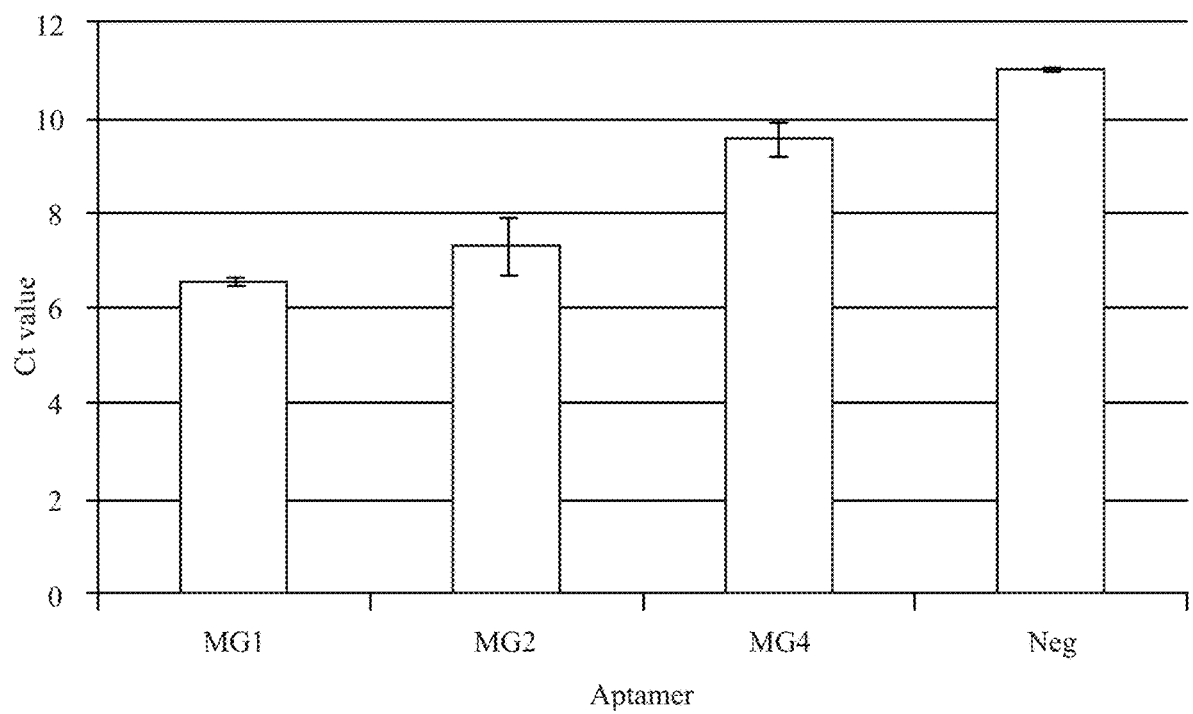

FIG. 4. Comparison of Ct values with different aptamers assessed for binding to *M. globosa*.

Figure 5:
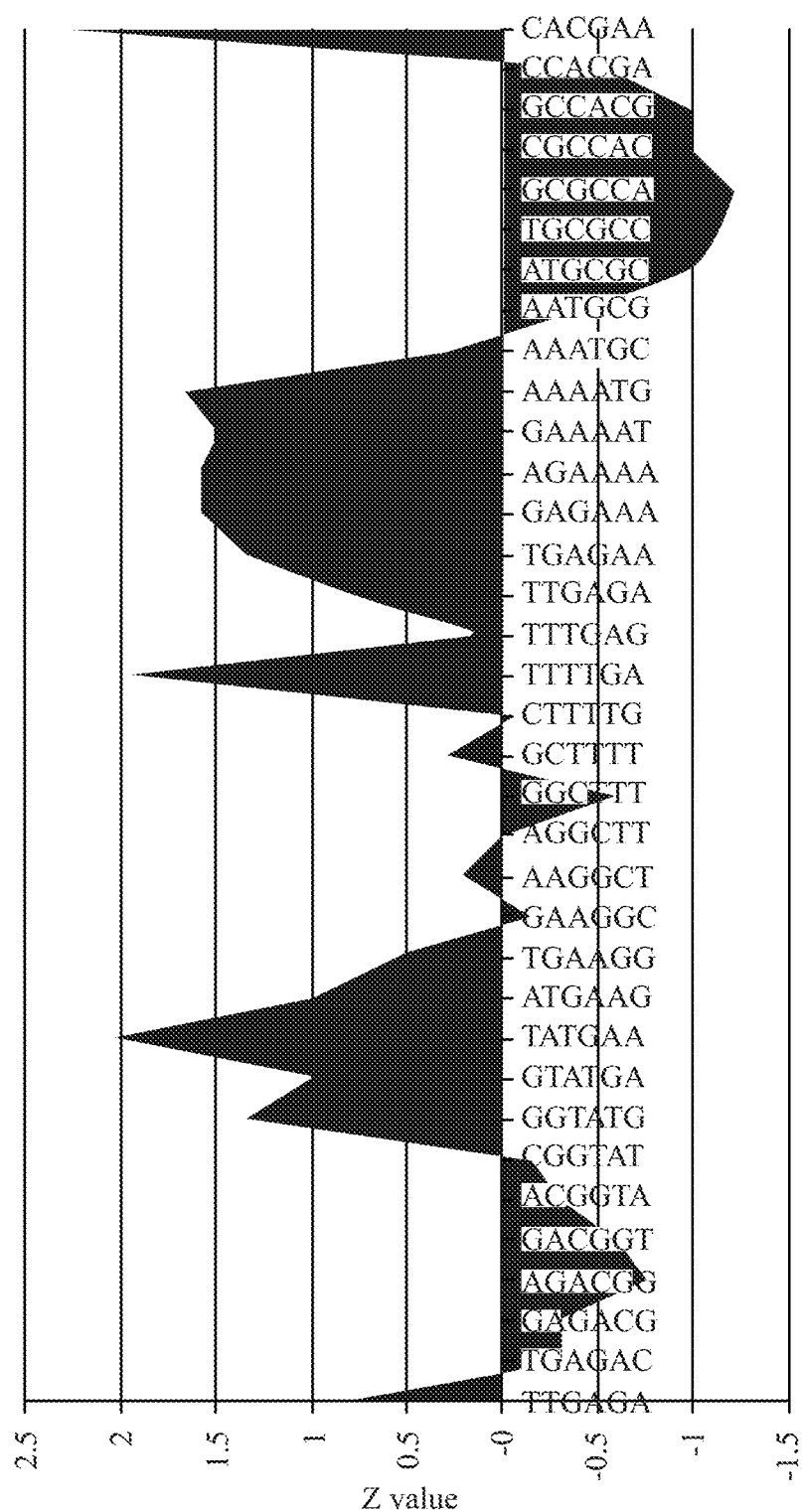

FIG. 5. Motif analysis of random region of aptamer Mg-1.

Figure 6:
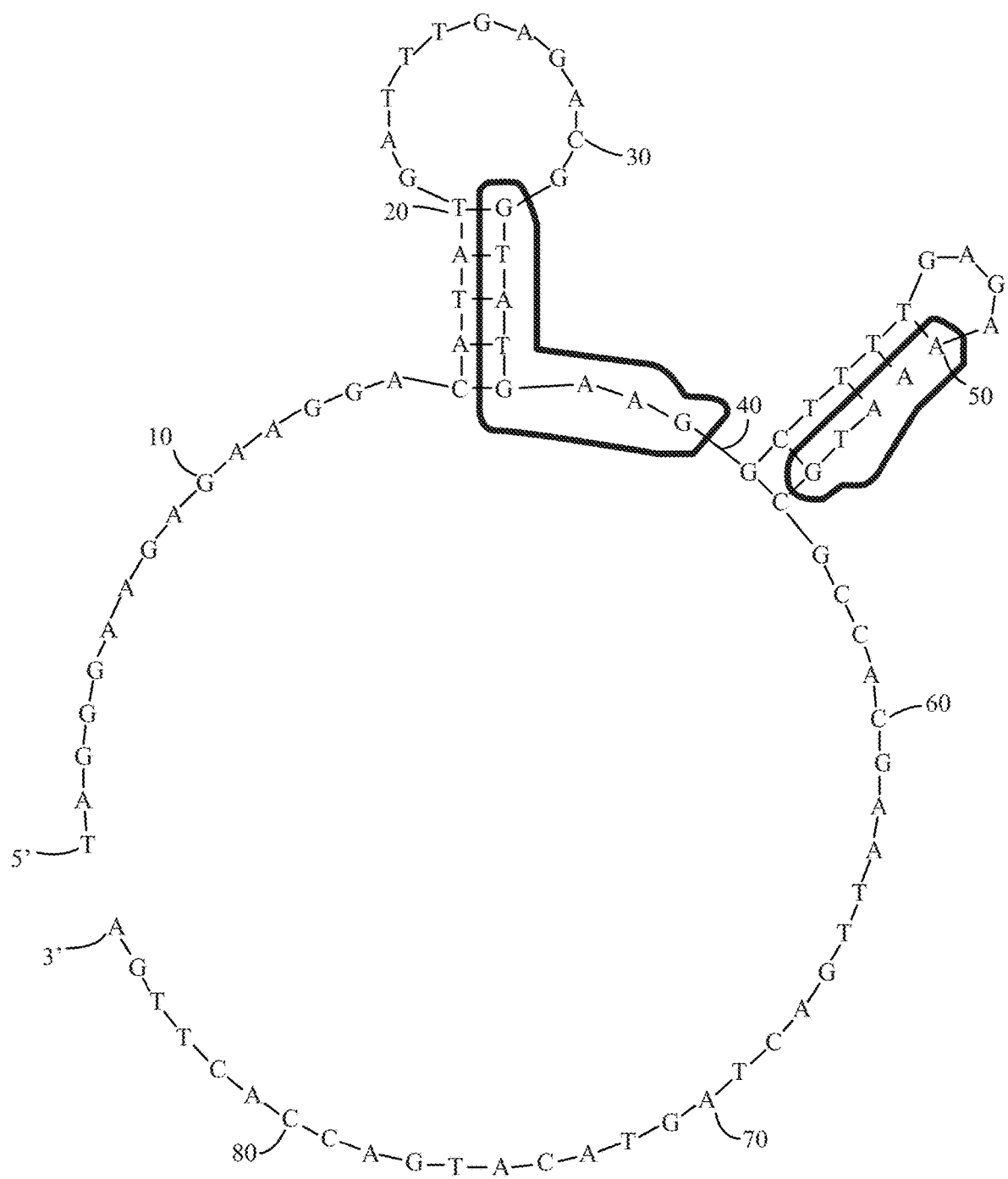

FIG. 6. The predicted secondary structures of aptamer Mg-1 and its conserved motifs.

Figure 7:
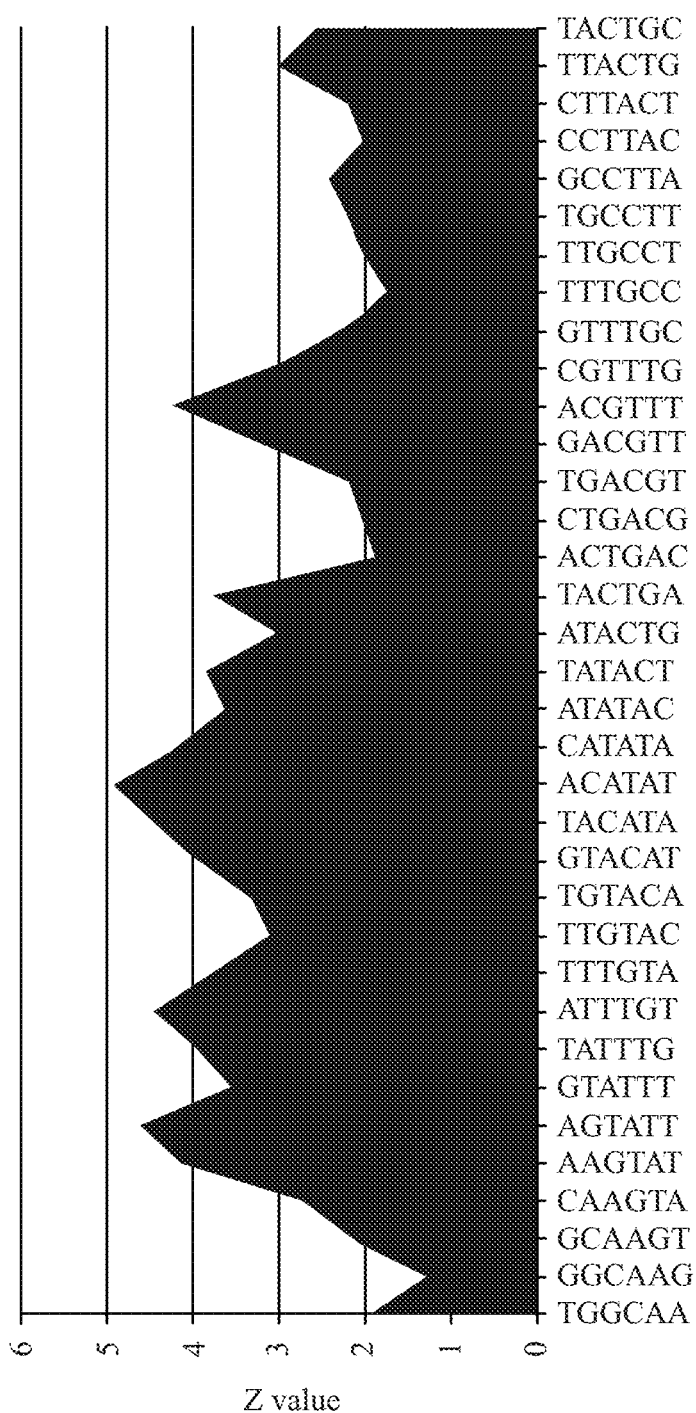

FIG. 7. Motif analysis of random region of aptamer Mg-2.

Figure 8:
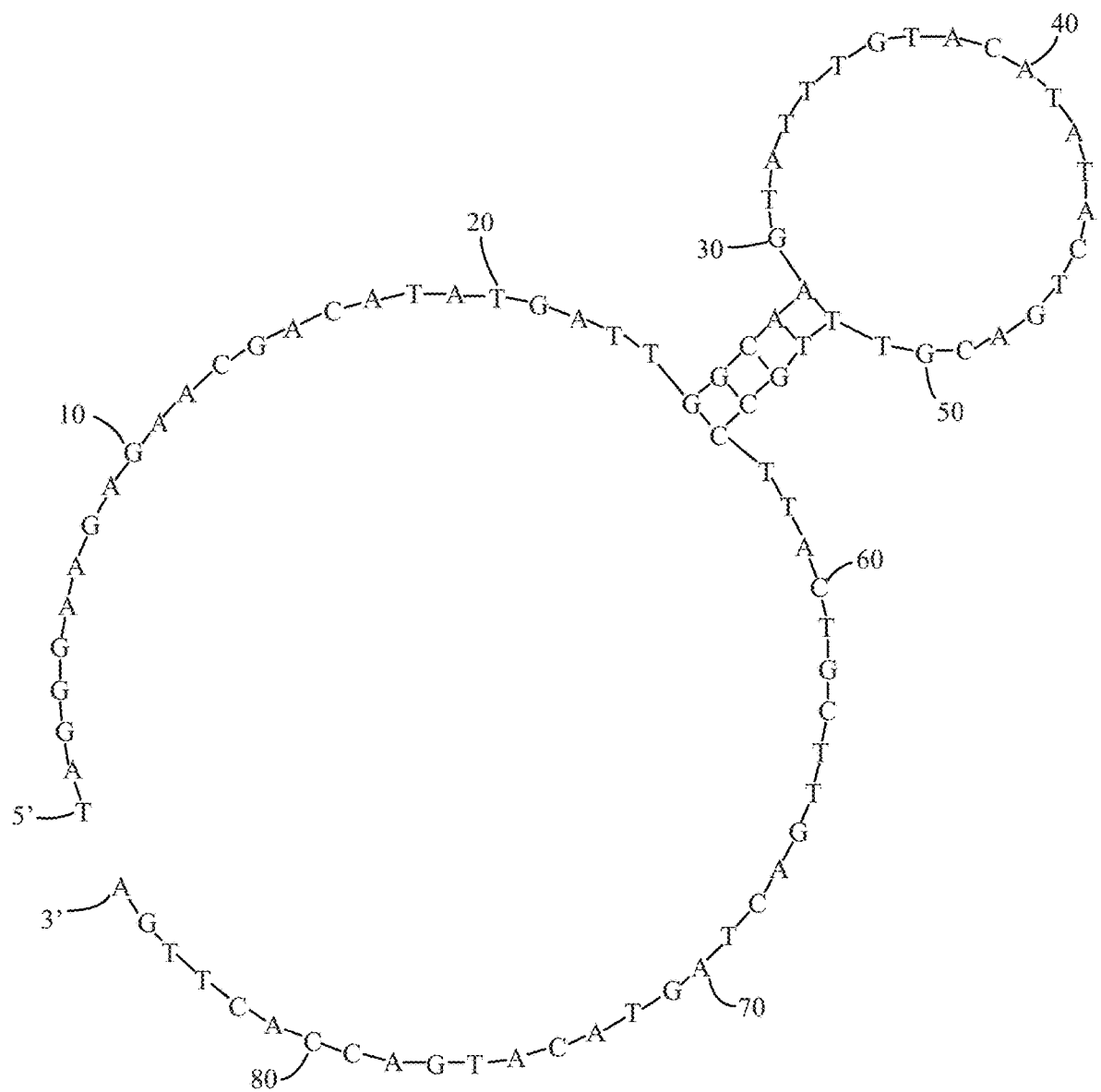

FIG. 8. Predicted secondary structure of aptamer Mg-2.

FIG. 9. Alignment of exemplary sequences with at least 90% nucleotide sequence identity that are identified during the selection process. Non-limiting examples of oligonucleotides with at least 90% nucleotide sequence identity to SEQ ID NO 5 are SEQ ID NO 23, SEQ ID NO 91, SEQ ID NO 92, and SEQ ID NO 95.

FIG. 10. Alignment of exemplary sequences with at least 70% nucleotide sequence identity that are identified during the selection process. Non-limiting examples of oligonucleotides with at least 70% nucleotide sequence identity to SEQ ID NO 4 are SEQ ID NO 20, SEQ ID NO 58, SEQ ID NO 72, SEQ ID NO 80, SEQ ID NO 43, SEQ ID NO 64, SEQ ID NO 65, and SEQ ID NO 71.

Figure 11:
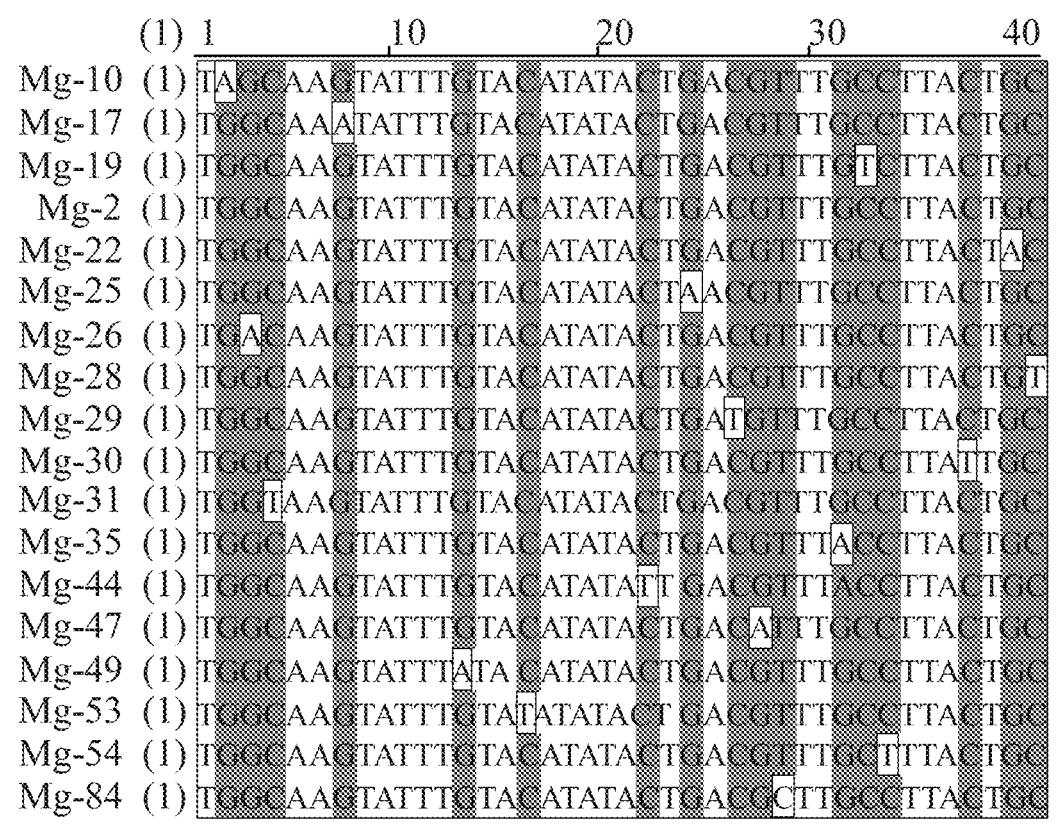

FIG. 11. Alignment of exemplary sequences with at least 50% nucleotide sequence identity that are identified during the selection process. Non-limiting examples of oligonucleotides with at least 50% nucleotide sequence identity to SEQ ID NO 2 are SEQ ID NO 84, SEQ ID NO 47, SEQ ID NO 17, SEQ ID NO 19, SEQ ID NO 25, SEQ ID NO 44, SEQ ID NO 49, SEQ ID NO 10, SEQ ID NO 30, SEQ ID NO 54, SEQ ID NO 29, SEQ ID NO 26, SEQ ID NO 35, SEQ ID NO 53, SEQ ID NO 22, SEQ ID NO 31, and SEQ ID NO 28.

DETAILED DESCRIPTION OF THE INVENTION

I. Definitions

As used herein, the term "aptamer" refers to a single stranded oligonucleotide or a peptide that has a binding affinity for a specific target.

As used herein, the term "nucleic acid" refers to a polymer or oligomer of nucleotides. Nucleic acids are also referred as "ribonucleic acids" when the sugar moiety of the nucleotides is D-ribose and as "deoxyribonucleic acids" when the sugar moiety is 2-deoxy-D-ribose.

As used herein, the term "nucleotide" usually refers to a compound consisting of a nucleoside esterified to a monophosphate, polyphosphate, or phosphate-derivative group via the hydroxyl group of the 5-carbon of the sugar moiety. Nucleotides are also referred as "ribonucleotides" when the sugar moiety is D-ribose and as "deoxyribonucleotides" when the sugar moiety is 2-deoxy-D-ribose.

As used herein, the term "nucleoside" refers to a glycosylamine consisting of a nucleobase, such as a purine or pyrimidine, usually linked to a 5-carbon sugar (e.g. D-ribose or 2-deoxy-D-ribose) via a β-glycosidic linkage. Nucleosides are also referred as "ribonucleosides" when the sugar moiety is D-ribose and as "deoxyribonucleosides" when the sugar moiety is 2-deoxy-D-ribose.

As used herein, the term "nucleobase", refers to a compound containing a nitrogen atom that has the chemical properties of a base. Non-limiting examples of nucleobases are compounds comprising pyridine, purine, or pyrimidine moieties, including, but not limited to adenine, guanine, hypoxanthine, thymine, cytosine, and uracil.

As used herein, the term "oligonucleotide" refers to an oligomer composed of nucleotides.

As used herein, the term "identical" or "sequence identity," in the context of two or more oligonucleotides, nucleic acids, or aptamers, refers to two or more sequences that are the same or have a specified percentage of nucleotides that are the same, when compared and aligned for maximum correspondence, as measured using sequence comparison algorithms or by visual inspection.

As used herein, the term "substantially homologous" or "substantially identical" in the context of two or more oligonucleotides, nucleic acids, or aptamers, generally refers to two or more sequences or subsequences that have at least 40%, 60%, 80%, 90%, 95%, 96%, 97%, 98% or 99% nucleotide identity, when compared and aligned for maximum correspondence, as measured using sequence comparison algorithms or by visual inspection.

As used herein, the term "epitope" refers to the region of a target that interacts with the aptamer. An epitope can be a contiguous stretch within the target or can be represented by multiple points that are physically proximal in a folded form of the target.

As used herein the term "binding affinity" may be calculated using the following equation: Binding Affinity=Amount of aptamer bound to one or more fungi species/Total amount of aptamer incubated with the one or more fungi species.

As used herein, the term "motif" refers to the sequence of contiguous, or series of contiguous, nucleotides occurring in a library of aptamers with binding affinity towards a specific target and that exhibits a statistically significant higher probability of occurrence than would be expected compared to a library of random oligonucleotides. The motif sequence is frequently the result or driver of the aptamer selection process.

II. Aptamer Compositions

Nucleic acid aptamers are single-stranded oligonucleotides with specific secondary and tertiary structures, that can bind to targets with high affinity and specificity. In the present invention, an aptamer composition may comprise at least one oligonucleotide consisting of deoxyribonucleotides, ribonucleotides, derivatives of deoxyribonucleotides, derivatives of ribonucleotides, and mixtures thereof, wherein said aptamer composition has a binding affinity for one or more fungi species from the genus *Malassezia*. In the present invention, said one or more fungi species may be selected from the group consisting of *M. globosa, M. furfur, M. restricta, M. caprae, M. cuniculi, M. dermatis, M. equine, M. japonica, M. nana, M. obtuse, M. pachydermatis, M. slooffiae, M. sympodialis, M. yamatoensis*, and mixtures thereof. In the present invention, said one or more fungi species may be selected from the group consisting of: *M. globosa, M. furfur, M. restricta*, and mixtures thereof.

In the present invention, said aptamer composition may comprise at least one oligonucleotide selected from the group consisting of oligonucleotides with at least 50% nucleotide sequence identity to sequences selected from the group consisting of SEQ ID NO 1 to SEQ ID NO 100. In the present invention, said aptamer composition may comprise at least one oligonucleotide selected from the group consisting of oligonucleotides with at least 70% nucleotide sequence identity to sequences selected from the group consisting of SEQ ID NO 1 to SEQ ID NO 100. In the present invention, said aptamer composition may comprise at least one oligonucleotide selected from the group consisting of oligonucleotides with at least 90% nucleotide sequence identity to sequences selected from the group consisting of SEQ ID NO 1 to SEQ ID NO 100. In the present invention, said aptamer composition may comprise at least one oligonucleotide selected from the group consisting of SEQ ID NO 1 to SEQ ID NO 100. In the present invention, said aptamer composition may comprise at least one oligonucleotide selected from the group consisting of oligonucleotides containing at least 10 contiguous nucleotides from sequences selected from the group consisting of SEQ ID NO 1 to SEQ ID NO 100. In the present invention, said aptamer composition may comprise at least one oligonucleotide selected from the group consisting of oligonucleotides containing at least 20 contiguous nucleotides from sequences selected from the group consisting of SEQ ID NO 1 to SEQ ID NO 100. In the present invention, said aptamer composition may comprise at least one oligonucleotide selected from the group consisting of oligonucleotides containing at least 40 contiguous nucleotides from sequences selected from the group consisting of SEQ ID NO 1 to SEQ ID NO 100. In the present invention, said aptamer composition may comprise at least one oligonucleotide selected from the group consisting of oligonucleotides containing at least 60 contiguous nucleotides from sequences selected from the group consisting of SEQ ID NO 1 to SEQ ID NO 100. In the present invention, said aptamer composition may comprise at least one oligonucleotide selected from the group consisting of oligonucleotides containing at least 70 contiguous nucleotides from sequences selected from the group consisting of SEQ ID NO 1 to SEQ ID NO 100. In the present invention, said aptamer composition may comprise at least one oligonucleotide selected from the group consisting of oligonucleotides containing at least 80 contiguous nucleotides from sequences selected from the group consisting of SEQ ID NO 1 to SEQ ID NO 100. A non-limiting example of oligonucleotides with at least 90% nucleotide sequence identity to SEQ ID NO 59 is SEQ ID NO 73. Non-limiting examples of oligonucleotides with at least 90% nucleotide sequence identity to SEQ ID NO 6 are SEQ ID NO 66, SEQ ID NO 74, SEQ ID NO 85, and SEQ ID NO 86. Non-limiting examples of oligonucleotides with at least 90% nucleotide sequence identity to SEQ ID NO 5 are SEQ ID NO 23, SEQ ID NO 91, SEQ ID NO 92, and SEQ ID NO 95 (see FIG. 9).

In the present invention, said aptamer composition may comprise at least one oligonucleotide selected from the group consisting of SEQ ID NO 1, SEQ ID NO 2, and SEQ ID NO 4. In the present invention, said aptamer composition may comprise at least one oligonucleotide selected from the group consisting of oligonucleotides with at least 50% nucleotide sequence identity to sequences selected from the group consisting of SEQ ID NO 1, SEQ ID NO 2, and SEQ ID NO 4. In the present invention, said aptamer composition may comprise at least one oligonucleotide selected from the group consisting of oligonucleotides with at least 70% nucleotide sequence identity to sequences selected from the group consisting of SEQ ID NO 1, SEQ ID NO 2, and SEQ ID NO 4. In the present invention, said aptamer composition may comprise at least one oligonucleotide selected from the group consisting of oligonucleotides with at least 90% nucleotide sequence identity to sequences selected from the group consisting of SEQ ID NO 1, SEQ ID NO 2, and SEQ ID NO 4. Non-limiting examples of oligonucleotides with at least 50% nucleotide sequence identity to SEQ ID NO 2 are SEQ ID NO 84, SEQ ID NO 47, SEQ ID NO 17, SEQ ID NO 19, SEQ ID NO 25, SEQ ID NO 44, SEQ ID NO 49, SEQ ID NO 10, SEQ ID NO 30, SEQ ID NO 54, SEQ ID NO 29, SEQ ID NO 26, SEQ ID NO 35, SEQ ID NO 53, SEQ ID NO 22, SEQ ID NO 31, and SEQ ID NO 28 (see FIG. 11). Non-limiting examples of oligonucleotides with at least 70% nucleotide sequence identity to SEQ ID NO 4 are SEQ ID NO 20, SEQ ID NO 58, SEQ ID NO 72, SEQ ID NO 80, SEQ ID NO 43, SEQ ID NO 64, SEQ ID NO 65, and SEQ ID NO 71 (see FIG. 10).

In the present invention, said at least one oligonucleotide comprises one or more motifs selected from the group consisting of SEQ ID NO 101, SEQ ID NO 102, and SEQ ID NO 103. In the present invention, said aptamer composition may comprise at least one oligonucleotide comprising a sequence of nucleotides with at least 70% nucleotide sequence identity to sequences selected from the group consisting of SEQ ID NO 101, SEQ ID NO 102, and SEQ ID NO 103. In the present invention, said aptamer composition may comprise at least one oligonucleotide comprising a sequence of nucleotides with at least 80% nucleotide sequence identity to sequences selected from the group consisting of SEQ ID NO 101, SEQ ID NO 102, and SEQ ID NO 103. In the present invention, said aptamer composition may comprise at least one oligonucleotide comprising a sequence of nucleotides with at least 90% nucleotide sequence identity to sequences selected from the group consisting of SEQ ID NO 101, SEQ ID NO 102, and SEQ ID NO 103.

Chemical modifications can introduce new features into the aptamers such as different molecular interactions with the target, improved binding capabilities, enhanced stability of oligonucleotide conformations, or increased resistance to nucleases. In the present invention, said at least one oligonucleotide of said aptamer composition may comprise natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, bromouracil, 5-iodouracil, and mixtures thereof.

Modifications of the phosphate backbone of the oligonucleotides can also increase the resistance against nuclease digestion. In the present invention, the nucleosides of said oligonucleotides may be linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In the present invention, the nucleosides of said oligonucleotides may be linked by natural phosphate diesters.

In the present invention, the sugar moiety of the nucleosides of said oligonucleotides may be selected from the group comprising ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N,N-dimethylacetamidyl ribose, N-morpholinophosphordiamidate, α-deoxyribofuranosyl, other pentoses, hexoses, and mixtures thereof.

In the present invention, said derivatives of ribonucleotides or said derivatives of deoxyribonucleotides may be selected from the group comprising: locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

In the present invention, the nucleotides at the 5'- and 3'-ends of said at least one oligonucleotide may be inverted. In the present invention, at least one nucleotide of said at least one oligonucleotide may be fluorinated at the 2' position of the pentose group. In the present invention, the pyrimidine nucleotides of said at least one oligonucleotide may be fluorinated at the 2' position of the pentose group. In the present invention, said aptamer composition may comprise at least one polymeric material, wherein said at least one polymeric material is covalently linked to said at least one oligonucleotide. In the present invention, said at least one polymeric material may be polyethylene glycol.

In the present invention, said at least one oligonucleotide may be between about 10 and about 200 nucleotides in length. In the present invention, said at least one oligonucleotide may be less than about 100 nucleotides in length. In the present invention, said at least one oligonucleotide may be less than about 50 nucleotides in length.

In the present invention, said at least one oligonucleotide may be covalently or non-covalently attached to one or more personal care active ingredients. In the present invention, said one or more personal care active ingredients may be selected from the group comprising anti-fungal agents, cooling agents, natural extracts, peptides, enzymes, and mixtures thereof. Suitable personal care active ingredients include any material that is generally considered as safe and that provides benefits to the skin, the scalp, or the hair.

Examples of conditions these actives address include, but are not limited to, dandruff, seborrhoeic dermatitis, tinea versicolor (pityriasis versicolor), and pityrosporum folliculitis. In the present invention, said one or more personal care active ingredients may be selected from the group consisting of antifungal agents. In the present invention, said one or more personal care active ingredients may be selected from the group consisting of zinc pyrithione, piroctone olamine, ketoconazole, and selenium disulfide.

In the present invention, said at least one oligonucleotide may be non-covalently attached to said one or more personal care active ingredients via molecular interactions. Examples of molecular interactions are electrostatic forces, van der Waals interactions, hydrogen bonding, and π-π stacking interactions of aromatic rings.

In the present invention, said at least one oligonucleotide may be covalently attached to said one or more personal care active ingredients using one or more linkers or spacers. Non-limiting examples of linkers are chemically labile linkers, enzyme-labile linkers, and non-cleavable linkers. Examples of chemically labile linkers are acid-cleavable linkers and disulfide linkers. Acid-cleavable linkers take advantage of low pH to trigger hydrolysis of an acid-cleavable bond, such as a hydrazone bond, to release the active ingredient or payload. Disulfide linkers can release the active ingredients under reducing environments. Examples of enzyme-labile linkers are peptide linkers that can be cleaved in the present of proteases and β-glucuronide linkers that are cleaved by glucuronidases releasing the payload. Non-cleavable linkers can also release the active ingredient if the aptamer is degraded by nucleases.

In the present invention, said at least one oligonucleotide may be covalently or non-covalently attached to one or more nanomaterials. In the present invention, said at least one oligonucleotide and said one or more personal care active ingredients may be covalently or non-covalently attached to one or more nanomaterials. In the present invention, said one or more personal care active ingredients may be carried by said one or more nanomaterials. Non-limiting examples of nanomaterials are gold nanoparticles, nano-scale iron oxides, carbon nanomaterials (such as single-walled carbon nanotubes and graphene oxide), mesoporous silica nanoparticles, quantum dots, liposomes, poly (lactide-co-glycolic acids) nanoparticles, polymeric micelles, dendrimers, serum albumin nanoparticles, and DNA-based nanomaterials. These nanomaterials can serve as carriers for large volumes of personal care active ingredients, while the aptamers can facilitate the delivery of the nanomaterials with the actives to the expected target.

Nanomaterials can have a variety of shapes or morphologies. Non-limiting examples of shapes or morphologies are spheres, rectangles, polygons, disks, toroids, cones, pyramids, rods/cylinders, and fibers. In the context of the present invention, nanomaterials usually have at least one spatial dimension that is less than about 100 μm and more preferably less than about 10 μm. Nanomaterials comprise materials in solid phase, semi-solid phase, or liquid phase.

Aptamers can also be peptides that bind to targets with high affinity and specificity. These peptide aptamers can be part of a scaffold protein. Peptide aptamers can be isolated from combinatorial libraries and improved by directed mutation or rounds of variable region mutagenesis and selection. In the present invention, said aptamer composition may comprise at least one peptide or protein; wherein said aptamer composition has a binding affinity for one or more fungi species from the genus *Malassezia*. In the present invention, said one or more fungi species may be selected from the group consisting of: *M. globosa, M. furfur, M. restricta, M. caprae, M. cuniculi, M. dermatis, M. equine, M. japonica, M. nana, M. obtuse, M. pachydermatis, M. sloofiae, M. sympodialis, M. yamatoensis*, and mixtures thereof. In the present invention, said one or more fungi species may be selected from the group consisting of: *M. globosa, M. furfur, M. restricta*, and mixtures thereof.

III. Methods of Designing Aptamer Compositions

The method of designing nucleic acid aptamers known as Systematic Evolution of Ligands by Exponential Enrichment (SELEX) has been broadly studied and improved for the selection of aptamers against small molecules and proteins (WO 91/19813). In brief, in the conventional version of SELEX, the process starts with the synthesis of a large library of oligonucleotides consisting of randomly generated sequences of fixed length flanked by constant 5'- and 3'-ends that serve as primers. The oligonucleotides in the library are then exposed to the target ligand and those that do not bind the target are removed. The bound sequences are eluted and amplified by PCR (polymerase chain reaction) to prepare for subsequent rounds of selection in which the stringency of the elution conditions is usually increased to identify the tightest-binding oligonucleotides. In addition to conventional SELEX, there are improved versions such as capillary electrophoresis-SELEX, magnetic bead-based SELEX, cell-SELEX, automated SELEX, complex-target SELEX, among others. A review of aptamer screening methods is found in (1) Kim, Y. S. and M. B. Gu, "Advances in Aptamer Screening and Small Molecule Aptasensors", Adv. Biochem. Eng. Biotechnol., 2014 140:29-67 (Biosensors based on Aptamers and Enzymes) and (2) Stoltenburg, R., et al. (2007) "SELEX-A (r)evolutionary method to generate high-affinity nucleic acid ligands" Biomol. Eng. 2007 24(4): 381-403, the contents of which are incorporated herein by reference. Although the SELEX method has been broadly applied, it is neither predictive nor standardized for every target. Instead, a method must be developed for each particular target in order for the method to lead to viable aptamers.

Despite the large number of selected aptamers, SELEX has not been routinely applied for the selection of aptamers with binding affinities towards macroscopic materials and surfaces. For the successful selection of aptamers with high binding affinity and specificity against macroscopic materials, the epitope should be present in sufficient amount and purity to minimize the enrichment of unspecifically binding oligonucleotides and to increase the specificity of the selection. Also, the presence of positively charged groups (e.g. primary amino groups), the presence of hydrogen bond donors and acceptors, and planarity (aromatic compounds) facilitate the selection of aptamers. In contrast, negatively charged molecules (e.g. containing phosphate groups) make the selection process more difficult. Unexpectedly, the inventors have found that SELEX can be used for the design of aptamers with high binding affinity and specificity for species of the genus *Malassezia*.

Selection Library

In SELEX, the initial candidate library is generally a mixture of chemically synthesized DNA oligonucleotides, each comprising a long variable region of n nucleotides flanked at the 3' and 5' ends by conserved regions or primer recognition regions for all the candidates of the library. These primer recognition regions allow the central variable region to be manipulated during SELEX in particular by means of PCR.

The length of the variable region determines the diversity of the library, which is equal to 4n since each position can be occupied by one of four nucleotides A, T, G or C. For long variable regions, huge library complexities arise. For instance, when n=50, the theoretical diversity is 450 or 1030, which is an inaccessible value in practice as it corresponds to more than 105 tons of material for a library wherein each sequence is represented once. The experimental limit is around 1015 different sequences, which is that of a library wherein all candidates having a variable region of 25 nucleotides are represented. If one chooses to manipulate a library comprising a 30-nucleotide variable region whose theoretical diversity is about 1018, only 1/1000 of the possibilities will thus be explored. In practice, that is generally sufficient to obtain aptamers having the desired properties. Additionally, since the polymerases used are unreliable and introduce errors at a rate on the order of 10-4, they contribute to significantly enrich the diversity of the sequence pool throughout the SELEX process. One candidate in 100 will be modified in each amplification cycle for a library with a random region of 100 nucleotides in length, thus leading to the appearance of 1013 new candidates for the overall library.

In the present invention, the starting mixture of oligonucleotides may comprise more than about 106 different oligonucleotides and more preferably between about 1013 to about 1015 different oligonucleotides. In the present invention, the length of the variable region may be between about 10 and about 100 nucleotides. In the present invention, the length of the variable region may be between about 20 and about 60 nucleotides. In the present invention, the length of the variable region may be about 40 nucleotides. Random regions shorter than 10 nucleotides may be used, but may be constrained in their ability to form secondary or tertiary structures and in their ability to bind to target molecules. Random regions longer than 100 nucleotides may also be used but may present difficulties in terms of cost of synthesis. The randomness of the variable region is not a constraint of the present invention. For instance, if previous knowledge exists regarding oligonucleotides that bind to a given target, libraries spiked with such sequences may work as well or better than completely random ones.

In the design of primer recognition sequences, care should be taken to minimize potential annealing among sequences, fold back regions within sequences, or annealing of the same sequence itself. In the present invention, the length of primer recognition sequences may be between about 10 and about 40 nucleotides. In the present invention, the length of primer recognition sequences may be between about 12 and about 30 nucleotides. In the present invention, the length of primer recognition sequences may be between about 18 and about 26 nucleotides, i.e., about 18, 19, 20, 21, 22, 23, 24, 25 or 26 nucleotides. The length and sequence of the primer recognition sequences determine their annealing temperature. In the present invention, the primer recognition sequences of said oligonucleotides may have an annealing temperature between about 60° C. and about 72° C.

Aptamers can be ribonucleotides (RNA), deoxynucleotides (DNA), or their derivatives. When aptamers are ribonucleotides, the first SELEX step may consist in transcribing the initial mixture of chemically synthesized DNA oligonucleotides via the primer recognition sequence at the 5' end. After selection, the candidates are converted back into DNA by reverse transcription before being amplified. RNA and DNA aptamers having comparable characteristics have been selected against the same target and reported in the art. Additionally, both types of aptamers can be competitive inhibitors of one another, suggesting potential overlapping of interaction sites.

New functionalities, such as hydrophobicity or photoreactivity, can be incorporated into the oligonucleotides by modifications of the nucleobases before or after selection. Modifications at the C-5 position of pyrimidines or at the C-8 or N-7 positions of purines are especially common and compatible with certain enzymes used during the amplification step in SELEX. In the present invention, said oligonucleotides may comprise natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, 5-bromouracil, 5-iodouracil, and mixtures thereof. Some non-natural nucleobases, such as 5-bromouracil or 5-iodouracil, can be used to generate photo-crosslinkable aptamers, which can be activated by UV light to form a covalent link with the target.

In the present invention, the nucleosides of said oligonucleotides may be linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In the present invention, the nucleosides of said oligonucleotides may be linked by natural phosphate diesters.

In the present invention, the sugar moiety of the nucleosides of said oligonucleotides may be selected from the group comprising ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N,N-dimethylacetamidyl ribose, N-morpholinophosphordiamidate, α-deoxyribofuranosyl, other pentoses, hexoses, and mixtures thereof.

In the present invention, said derivatives of ribonucleotides or said derivatives of deoxyribonucleotides may be selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

When using modified nucleotides during the SELEX process, they should be compatible with the enzymes used during the amplification step. Non-limiting examples of modifications that are compatible with commercial enzymes include modifications at the 2' position of the sugar in RNA libraries. The ribose 2'-OH group of pyrimidine nucleotides can be replaced with 2'-amino, 2'-fluoro, 2'-methyl, or 2'-O-methyl, which protect the RNA from degradation by nucleases. Additional modifications in the phosphate linker, such as phosphorothionate and boranophosphate, are also compatible with the polymerases and confer resistance to nucleases.

In the present invention, at least one nucleotide of said oligonucleotides may be fluorinated at the 2' position of the pentose group. In the present invention, the pyrimidine nucleotides of said oligonucleotides may be at least partially fluorinated at the 2' position of the pentose group. In the present invention, all the pyrimidine nucleotides of said oligonucleotides may be fluorinated at the 2' position of the pentose group. In the present invention, at least one nucleotide of said oligonucleotides may be aminated at the 2' position of the pentose group.

Another approach, recently described as two-dimensional SELEX, simultaneously applies in vitro oligonucleotide selection and dynamic combinatorial chemistry (DCC), e.g., a reversible reaction between certain groups of the oligonucleotide (amine groups) and a library of aldehyde compounds. The reaction produces imine oligonucleotides, which are selected on the same principles as for conventional SELEX. It is thus possible to identify for a target hairpin RNA modified aptamers that differ from natural aptamers.

A very different approach relates to the use of optical isomers. Natural oligonucleotides are D-isomers. L-analogs are resistant to nucleases but cannot be synthesized by polymerases. According to the laws of optical isomerism, an L-series aptamer can form with its target (T) a complex having the same characteristics as the complex formed by the D-series isomer and the enantiomer (T') of the target (T). Consequently, if compound T' can be chemically synthesized, it can be used to perform the selection of a natural aptamer (D). Once identified, this aptamer can be chemically synthesized in an L-series. This L-aptamer is a ligand of the natural target (T).

Selection Step

Single stranded oligonucleotides can fold to generate secondary and tertiary structures, resembling the formation of base pairs. The initial sequence library is thus a library of three-dimensional shapes, each corresponding to a distribution of units that can trigger electrostatic interactions, create hydrogen bonds, etc. Selection becomes a question of identifying in the library the shape suited to the target, i.e., the shape allowing the greatest number of interactions and the formation of the most stable aptamer-target complex. For small targets (dyes, antibiotics, etc.) the aptamers identified are characterized by equilibrium dissociation constants in the micromolar range, whereas for protein targets Kd values below 10-9 M are not rare.

Selection in each round occurs by means of physical separation of oligonucleotides associated with the target from free oligonucleotides. Multiple techniques may be applied (chromatography, filter retention, electrophoresis, etc.). The selection conditions are adjusted (relative concentration of target/candidates, ion concentration, temperature, washing, etc.) so that a target-binding competition occurs between the oligonucleotides. Generally, stringency is increased as the rounds proceed in order to promote the capture of oligonucleotides with the highest affinity. In addition, counter-selections or negative selections are carried out to eliminate oligonucleotides that recognize the support or unwanted targets (e.g., filter, beads, etc.).

The SELEX process for the selection of target-specific aptamers is characterized by repetition of five main steps: (1) binding of oligonucleotides to the target, (2) partition or removal of oligonucleotides with low binding affinity, (3) elution of oligonucleotides with high binding affinity, (4) amplification or replication of oligonucleotides with high binding affinity, and (5) conditioning or preparation of the oligonucleotides for the next cycle. This selection process is designed to identify the oligonucleotides with the greatest affinity and specificity for the target material.

In the present invention, a method of designing an aptamer composition may comprise the step of contacting: a) a mixture of oligonucleotides, b) a selection buffer, and c) a target material selected from the group consisting one or more fungi species from the genus *Malassezia*. In the present invention, said one or more fungi species may be selected from the group consisting of: *M. globosa, M. furfur, M. restricta, M. caprae, M. cuniculi, M. dermatis, M. equine, M. japonica, M. nana, M. obtuse, M. pachydermatis, M. slooffiae, M. sympodialis, M. yamatoensis*, and mixtures thereof. In the present invention, said one or more fungi species may be selected from the group consisting of: *M. globosa, M. furfur, M. restricta*, and mixtures thereof. In the present invention, said mixture of oligonucleotides may comprise oligonucleotides selected from the group consisting of deoxyribonucleotides, ribonucleotides, derivatives of deoxyribonucleotides, derivatives of ribonucleotides, and mixtures thereof.

SELEX cycles are usually repeated several times until oligonucleotides with high binding affinity are identified. The number of cycles depends on multiple variables, including target features and concentration, design of the starting random oligonucleotide library, selection conditions, ratio of target binding sites to oligonucleotides, and the efficiency of the partitioning step. In the present invention, said contacting step may be performed at least 5 times. In the present invention, said contacting step may be performed between 6 and 15 times. In the present invention, said method further may comprise the step of removing the oligonucleotides that do not bind said target material during said contacting step.

Oligonucleotides are oligo-anions, each unit having a charge and hydrogen-bond donor/acceptor sites at a particular pH. Thus, the pH and ionic strength of the selection buffer are important and should represent the conditions of the intended aptamer application. In the present invention, the pH of said selection buffer may be between about 2 and about 9. In the present invention, the pH of said selection buffer may be between about 5 and about 8.

Cations do not only facilitate the proper folding of the oligonucleotides, but also can provide benefits to the hair or the scalp. In the present invention, said selection buffer may comprise cations. Non-limiting examples of cations are $Zn^{2+}$, $Cu^{2+}$. In the present invention, said selection buffer may comprise divalent cations selected from the group comprising $Zn^{2+}$ and $Cu^{2+}$.

In order for the aptamers to maintain their structures and function during their application, the in vitro selection process can be carried out under conditions similar to those for which they are being developed. In the present invention, said selection buffer may comprise a solution or suspension of a personal care composition selected from the group comprising shampoos, conditioning shampoos, pet shampoo, leave-in treatments, sprays, liquids, pastes, Newtonian or non-Newtonian fluids, gels, and sols. In the present invention, said selection buffer may comprise a solution of a shampoo chassis.

In the present invention, said selection buffer may comprise at least one surfactant. In the present invention, said at least one surfactant may be selected from the group consisting of anionic surfactants, amphoteric or zwitterionic surfactants, and mixtures thereof. Non-limiting examples of anionic surfactants are alkyl and alkyl ether sulfates or sulfonates, including ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. Non-limiting amphoteric surfactants include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate, including cocoamphoacetate, cocoamphodiacetate, lauroamphoacetate, lauroamphodiacetate, and mixtures thereof. Non-limiting examples of zwitterionic surfactants include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate, and betains.

In the present invention, said selection buffer may comprise at least one material selected from the group comprising: aqueous carriers, gel matrixes, silicone conditioning agents, organic conditioning materials, non-ionic polymers, deposition aids, rheology modifier/suspending agents, benefit agents, and mixtures thereof. Non-limiting examples of aqueous carriers are water and water solutions of lower alkyl alcohols and polyhydric alcohols, including ethanol, isopropanol, propylene glycol, hexylene glycol, glycerin, and propane diol. Non-limiting examples of gel matrixes include water solutions of fatty alcohols, including cetyl alcohol, stearyl alcohol, behenyl alcohol, and mixtures thereof. Non-limiting examples of silicone conditioning agents include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, sugar or polysaccharide groups, fluorine-modified alkyl groups, alkoxy groups, or combinations of such groups. Non-limiting examples of organic conditioning materials include hydrocarbon oils, polyolefins, fatty esters, fluorinated conditioning compounds, fatty alcohols, alkyl glucosides and alkyl glucoside derivatives, quaternary ammonium compounds, polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof. Non-limiting examples of non-ionic polymers include polyalkylene glycols, such as polyethylene glycols. Non-limiting examples of deposition aids include copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone; vinyl esters, vinyl alcohol (made by hydrolysis of polyvinyl acetate), maleic anhydride, propylene glycol, and ethylene glycol, cationic celluloses, cationic starches, and cationic guar gums. Non-limiting examples of rheology modifier/suspending agents include homopolymers based on acrylic acid, methacrylic acid or other related derivatives, alginic acid-based materials, and cellulose derivatives. Non-limiting examples of benefit agents include brightening agents, strengthening agents, anti-fungal agents, anti-bacterial agents, anti-microbial agents, anti-dandruff agents, anti-malodor agents, perfumes, olfactory enhancement agents, anti-itch agents, cooling agents, anti-adherence agents, moisturization agents, smoothness agents, surface modification agents, antioxidants, natural extracts and essential oils, dyes, pigments, bleaches, nutrients, peptides, vitamins, enzymes, chelants, and mixtures thereof.

Negative selection or counter-selection steps can minimize the enrichment of oligonucleotides that bind to undesired targets or undesired epitopes within a target. In the present invention, said method of designing an aptamer composition may further comprise the step of contacting: a) a mixture of oligonucleotides, b) a selection buffer, and c) one or more undesired targets. Methods for negative selection or counter-selection of aptamers against unbound targets have been published in WO201735666, the content of which is incorporated herein by reference.

In the present invention, the method of designing an aptamer composition may comprise the steps of: a) synthesizing a mixture of oligonucleotides; b) contacting: i. said mixture of oligonucleotides, ii. a selection buffer, and iii. a target material selected from the group consisting of: *M. globosa, M. furfur, M. restricta*, and mixtures thereof, to produce a target suspension; c) removing the liquid phase from said target suspension to produce a target-oligonucleotide mixture; d) contacting said target-oligonucleotide mixture with a washing buffer and removing the liquid phase to produce a target-aptamer mixture; and e) contacting said target-aptamer mixture with an elution buffer and recovering the liquid phase to produce an aptamer mixture. In the present invention, said steps may be performed repetitively at least 5 times. In the present invention, said steps may be performed between 6 and 15 times.

In the present invention, the method of designing an aptamer composition may comprise the steps of: a) synthesizing a random mixture of deoxyribonucleotides comprising oligonucleotides consisting of: i. a T7 promoter sequence at the 5'-end, ii. a variable 40-nucleotide sequence in the middle, and iii. a conserved reverse primer recognition sequence at the 3'end; b) contacting: i. said random mixture of deoxyribonucleotides, ii. a selection buffer, and iii. a suspension of *M. globosa*, to produce a target suspension; c) removing the liquid phase from said target suspension to produce a hair-oligonucleotide mixture; d) contacting said hair-oligonucleotide mixture with a washing buffer and removing the liquid phase to produce a hair-aptamer mixture; e) contacting said hair-aptamer mixture with an elution buffer and recovering the liquid phase to produce a DNA aptamer mixture; f) amplifying said DNA aptamer mixture to produce an enriched mixture of deoxyribonucleotides; and g) sequencing said enriched mixture of deoxyribonucleotides.

Post-Selection Modification

To enhance stability of the aptamers, chemical modifications can be introduced in the aptamer after the selection process. For instance, the 2'-OH groups of the ribose moieties can be replaced by 2'-fluoro, 2'-amino, or 2'-O-methyl groups. Furthermore, the 3'- and 5'-ends of the aptamers can be capped with different groups, such as streptavidin-biotin, inverted thymidine, amine, phosphate, polyethylene-glycol, cholesterol, fatty acids, proteins, enzymes, fluorophores, among others, making the oligonucleotides resistant to exonucleases or providing some additional benefits. Other modifications are described in previous sections of the present disclosure.

Unlike backbone modifications which can cause aptamer-target interaction properties to be lost, it is possible to conjugate various groups at one of the 3'- or 5'-ends of the oligonucleotide in order to convert it into a delivery vehicle, tool, probe, or sensor without disrupting its characteristics. This versatility constitutes a significant advantage of aptamers, in particular for their application in the current invention. In the present invention, one or more personal care active ingredients may be covalently attached to the 3'-end of said at least one oligonucleotide. In the present invention, one or more personal care active ingredients may be covalently attached to the 5'-end of said at least one oligonucleotide. In the present invention, one or more personal care active ingredients may be covalently attached to random positions of said at least one oligonucleotide.

Incorporation of modifications to aptamers can be performed using enzymatic or chemical methods. Non-limiting examples of enzymes used for modification of aptamers are terminal deoxynucleotidyl transferases (TdT), T4 RNA ligases, T4 polynucleotide kinases (PNK), DNA polymerases, RNA polymerases, and other enzymes known by those skilled in the art. TdTs are template-independent polymerases that can add modified deoxynucleotides to the 3' terminus of deoxyribonucleotides. T4 RNA ligases can be used to label ribonucleotides at the 3'-end by using appropriately modified nucleoside 3',5'-bisphosphates. PNK can be used to phosphorylate the 5'-end of synthetic oligonucleotides, enabling other chemical transformations (see below). DNA and RNA polymerases are commonly used for the random incorporation of modified nucleotides throughout the sequence, provided such nucleotides are compatible with the enzymes.

Non-limiting examples of chemical methods used for modification of aptamers are periodate oxidation of ribonucleotides, EDC activation of 5'-phosphate, random chemical labeling methods, and other chemical methods known by those skilled in the art, incorporated herein.

During periodate oxidation, meta- and ortho-periodates cleave the C—C bonds between vicinal diols of 3'-ribonucleotides, creating two aldehyde moieties that enable the conjugation of labels or active ingredients at the 3'-end of RNA aptamers. The resulting aldehydes can be easily reacted with hydrazide- or primary amine-containing molecules. When amines are used, the produced Schiff bases can be reduced to more stable secondary amines with sodium cyanoborohydride (NaBH4).

When EDC activation of 5'-phosphate is used, the 5'-phosphate of oligonucleotides is frequently activated with EDC (1-Ethyl-3-[3-dimethylaminopropyl]carbodiimide hydrochloride) and imidazole to produce a reactive imidazolide intermediate, followed by reaction with a primary amine to generate aptamers modified at the 5'end. Because the 5' phosphate group is required for the reaction, synthetic oligonucleotides can be first treated with a kinase (e.g. PNK).

Random chemical labeling can be performed with different methods. Because they allow labeling at random sites along the aptamer, a higher degree of modification can be achieved compared to end-labeling methods. However, since the nucleobases are modified, binding of the aptamers to their target can be disrupted. The most common random chemical modification methods involve the use of photoreactive reagents, such as phenylazide-based reagents. When the phenylazide group is exposed to UV light, it forms a labile nitrene that reacts with double bonds and C—H and N—H sites of the aptamers.

Additional information about methods for modification of aptamers is summarized in Hermanson G. T., "Bioconjugate Techniques", pp. 969-1002, 2nd Edition, Academic Press, San Diego, 2008, the content of which is incorporated herein by reference.

After selection, in addition to chemical modifications, sequence truncations can be performed to remove regions that are not essential for binding or for folding into the structure. Moreover, aptamers can be linked together to provide different features or better affinity. Thus, any truncations or combinations of the aptamers described herein are incorporated as part of the current invention.

IV. Application of Aptamer Compositions in Personal Care Products

The aptamers of the current invention can be used in hair care compositions to provide one or more benefits.

Shampoo Composition

The hair care composition of the present invention can be a shampoo. The shampoo composition comprises from about 0.001% to about 1%, alternatively from about 0.01% to about 0.5%, alternatively from about 0.1% to about 0.3% of one or more aptamer.

A. Detersive Surfactant

The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non-limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines may be selected.

Non-limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

B. Aqueous Carrier

The shampoo composition comprises an aqueous carrier. Accordingly, the formulations of the shampoo composition can be in the form of pourable liquids (under ambient conditions). Such compositions will therefore typically comprise an aqueous carrier, which is present at a level of at least 20 wt %, from about 20 wt % to about 95 wt %, or from about 60 wt % to about 85 wt %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Conditioner Composition

The hair care composition of the present invention can be a hair conditioner. The hair conditioner composition described herein comprises (i) from about 0.001% to about 1%, alternatively from about 0.01% to about 0.5%, alternatively from about 0.1% to about 0.3% of one or more aptamer. The conditioner composition may also comprise a conditioner gel matrix comprising (1) one or more high melting point fatty compounds, (2) a cationic surfactant system, and (3) a second aqueous carrier.

A. Cationic Surfactant System

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

Mono-Long Alkyl Quaternized Ammonium Salt

The monoalkyl quaternized ammonium salt cationic surfactants useful herein are those having one long alkyl chain which has about 22 carbon atoms and may be a C22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

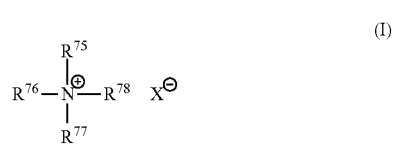

wherein one of R75, R76, R77 and R78 is selected from an alkyl group of 22 carbon atoms or an aromatic, alkoxy, polyoxyalkylene, alkylamido, hydroxyalkyl, aryl or alkylaryl group having up to about 30 carbon atoms; the remainder of R75, R76, R77 and R78 are independently selected from an alkyl group of from 1 to about 4 carbon atoms or an alkoxy, polyoxyalkylene, alkylamido, hydroxyalkyl, aryl or alkylaryl group having up to about 4 carbon atoms; and X— is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of R75, R76, R77 and R78 can be selected from an alkyl group of about 22 carbon atoms, the remainder of R75, R76, R77 and R78 are independently selected from CH3, C2H5, C2H4OH, and mixtures thereof; and X is selected from the group consisting of Cl, Br, CH3OSO3, C2H5OSO3, and mixtures thereof.

Nonlimiting examples of such mono-long alkyl quaternized ammonium salt cationic surfactants include: behenyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of about 22 carbons. Exemplary tertiary amido amines include: behenamidopropyldimethylamine, behenamidopropyldiethylamine, behenamidoethyldiethylamine, behenamidoethyldimethylamin. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; and may be l-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The di-long alkyl quaternized ammonium salt cationic surfactants useful herein are those having two long alkyl chains having about 22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

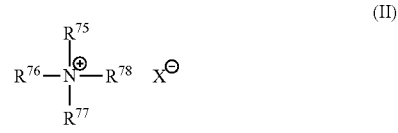

wherein two of R75, R76, R77 and R78 is selected from an alkyl group of from 22 carbon atoms or an aromatic, alkoxy, polyoxyalkylene, alkylamido, hydroxyalkyl, aryl or alkylaryl group having up to about 30 carbon atoms; the remainder of R75, R76, R77 and R78 are independently selected from an alkyl group of from 1 to about 4 carbon atoms or an alkoxy, polyoxyalkylene, alkylamido, hydroxyalkyl, aryl or alkylaryl group having up to about 4 carbon atoms; and X— is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of R75, R76, R77 and R78 can be selected from an alkyl group of from 22 carbon atoms, the remainder of R75, R76, R77 and R78 are independently selected from CH3, C2H5, C2H4OH, and mixtures thereof; and X is selected from the group consisting of Cl, Br, CH3OSO3, C2H5OSO3, and mixtures thereof.

Such dialkyl quaternized ammonium salt cationic surfactants include, for example, dialkyl (C22) dimethyl ammonium chloride, ditallow alkyl dimethyl ammonium chloride, dihydrogenated tallow alkyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

C. Aqueous Carrier

The conditioner gel matrix of the conditioner composition includes an aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Leave-on Treatment

The hair care composition of the present invention can be leave-on treatment. The leave-on treatment composition described herein may comprise from about 0.001% to about 1%, alternatively from about 0.01% to about 0.5%, alternatively from about 0.1% to about 0.3% of one or more aptamer. The leave-on treatment may also comprise (1) one or more rheology modifiers and (2) an aqueous carrier.

A. Rheology Modifier

The leave-on treatment may include one or more rheology modifiers to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. The leave-on treatment may comprise from about 0.01% to about 3% of a rheology modifier, alternatively from about 0.1% to about 1% of a rheology modifier, The one or more rheology modifier may be selected from the group consisting of polyacrylamide thickeners, cationically modified polysaccharides, associative thickeners, and mixtures thereof. Associative thickeners include a variety of material classes such as, for example: hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobically modified polyethers. These materials may have a hydrophobe that can be selected from cetyl, stearyl, oleayl, and combinations thereof, and a hydrophilic portion of repeating ethylene oxide groups with repeat units from 10-300, alternatively from 30-200, and alternatively from 40-150. Examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

Non-limiting examples of additional rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E 10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and/or combinations thereof.

B. Aqueous Carrier

The leave-on treatment may comprise an aqueous carrier. Accordingly, the formulations of the leave-on treatment can be in the form of pourable liquids (under ambient conditions). Such compositions will therefore typically comprise an aqueous carrier, which is present at a level of at least 20 wt %, from about 20 wt % to about 95 wt %, or from about 60 wt % to about 85 wt %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

pH

The hair care composition of the present invention may have a pH in the range from about 2 to about 10, at 25° C. More preferably, the hair care composition may have a pH in the range of from about 2 to about 6, alternatively from about 3.5 to about 5, alternatively from about 5.25 to about 7.

Additional Components

The hair care composition described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care composition may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The hair care compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Additional Benefit Agents

The hair care composition may further comprise one or more additional benefit agents. The benefit agents comprise a material selected from the group consisting of anti-dandruff agents, anti-fungal agents, anti-itch agents, anti-bacterial agents, anti-microbial agents, moisturization agents, antioxidants, vitamins, lipid soluble vitamins, perfumes, brighteners, enzymes, sensates, attractants, dyes, pigments, bleaches, and mixtures thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms.

The hair care compositions may be provided in the form of a porous, dissolvable solid structure, such as those disclosed in U.S. Patent Application Publication Nos. 2009/0232873; and 2010/0179083, which are incorporated herein by reference in their entirety. Accordingly, the hair care compositions comprise a chelant, a buffer system comprising an organic acid, from about 23% to about 75% surfactant; from about 10% to about 50% water soluble polymer; and optionally, from about 1% to about 15% plasticizer; such that the hair care composition is in the form of a flexible porous dissolvable solid structure, wherein said structure has a percent open cell content of from about 80% to about 100%.

The hair care compositions may be in the form of a viscous liquid comprising one or more aptomer, 20% surfactant and a polycarboxylate rheology modifier; wherein the polycarboxylate is specifically chosen to be effective at the high electrolyte levels resulting from the incorporation of the key buffer system and chelant used for this invention. Non-limiting examples include acrylates/C10-C30 alkyl acrylate crosspolymers such as Carbopol EDT2020, 1342, 1382, etc. from Lubrizol. Rheology benefits of these actives may include stability, ease of dispensing, smoothness of spreading, etc.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

Diagnostic Tool—Detectable Fungal Contamination

The aptamer of the present invention can be used in diagnostic methods for the detection of fungal contamination. The contaminations may be at the scalp, skin, foot, blood or other parts of the body. The aptamer of the present invention can be combined (covalently or not) with a detection agent such as fluorescent dye, a color dye, a pigment, an imaging agent, or another molecule or moiety that enables the presence of the specific fungus. After the complex of the fungus and the aptamer is formed, the detection of the complex may be directly apparent by the development of a color or other visible indication or it may need an analytical device to detect such as X-ray, spectroscopy, MRI, radionuclide methodology, etc. The separation of the native aptamer from the aptamer-fungus complex may be necessary or not.

The methodology of detecting the fungus enabled by the present invention can be very specific for the particular fungus as the aptamer is designed to bind the particular fungus selectively. Thus, the detection limits are expected to be very low. In addition, the methodology is relatively fast that common techniques that rely on culture of the fungus for its detection, which are very time consuming (at least a few hours or even days).

The diagnostic methods of the present invention can be used for the detection of the fungus in intravenous drugs or other drugs or in food sources or food preparations or in toys and other surfaces that may cause human or pet contamination. There are examples of severe health consequences, even deaths, which are caused by difficult-to-detect *Malassezia furfur* contamination of parenterals.

In the hair/scalp care field, the diagnostic method can involve detection of fungal infection using a kit, such as (a) a swab or (b) a woven substrate or (c) or nonwoven substrate or (d) comb, which comprise a region having an absorbing element comprising the aptamer and a detection agent for a simple and accurate detection of the fungus that causes dandruff. In the feminine protection field, the diagnostic method can involve detection of fungal infection using a kit, such as a swab or a comb or another substrate comb that comprises the aptamer and a detection agent for a simple and accurate detection of the fungus that causes vaginal Candidiasis. In the feminine protection field and in the diaper field, the diagnostic method can involve detection of fungal infection using a kit, such as a swab or a comb or another substrate comb that comprises the aptamer and a detection agent for a simple and accurate detection of the fungus that causes yeast infection.

EXAMPLES

The following examples illustrate non-limiting examples of the invention described herein. The exemplified hair care compositions can be prepared by conventional formulation and mixing techniques. It will be appreciated that other modifications of the hair care compositions within the skill of those in the formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of hair care compositions described herein.

Shampoo Composition Examples

| Ingredients | Shampoo Example 1 wt % | Shampoo Example 2 wt % |
|---|---|---|
| Water Purified | Q.S to 100 | Q.S to 100 |
| Sodium Laureth-3 Sulfate | 21.6 | 21.6 |
| Sodium Lauryl Sulfate | 34.5 | 34.5 |
| Laureth-4 | 0.9 | 0.9 |
| Dimethicone 330M cps | 0.5 | 0.5 |
| Glycol Distearate | 1.5 | 1.5 |
| Polyquaternium-6 | 0.32 | 0.32 |
| MG1 Aptamer | 0.01 | 0.001 |
| Sodium Benzoate | 0.27 | 0.27 |
| Citric acid 50% Solution | 0.52 | 0.52 |
| Methylchloroisothiazolinone/methylisothiazolinone | 0.035 | 0.035 |
| Sodium chloride | 1.66 | 1.66 |
| Fragrance | 0.65 | 0.65 |
| DL-Panthenol 56% solution | 0.05 | 0.05 |
| Panthenyl Ethyl ether | 0.03 | 0.03 |
| Glycol Distearate | 1.5 | 1.5 |

Additional Shampoo Examples

| Ingredient | SH Ex 3 | SH Ex 4 | SH Ex 5 | SH Ex 6 | SH Ex 7 | SH Ex 8 | SH Ex 9 |
|---|---|---|---|---|---|---|---|
| Sodium lauryl ether sulfate (SLE3S) | | 6 | 10 | 6 | 6 | 9 | |
| Sodium cocoyl isethionate | | | | | | | 8.5 |
| Sodium lauryl sulfate (SLS) | 1.5 | 7 | 1.5 | 7 | 7 | 6 | |
| Sodium lauryl ether sulfate (SLE1S) | 10.5 | | | | | | |
| Disodium laureth sulfosuccinate | | | | | | | 8.5 |
| Sodium lauryl sulfoacetate | | | | | | | 2.5 |
| Sodium Lauroyl Sarcosinate | | | | | | | 0.75 |
| Cocoamidopropyl Hydroxysultaine | | | | | | | 1.5 |
| Cocoamidopropyl Betaine | 1 | 2 | 2 | 2 | 2 | 2 | 2 |
| Coconut monoethanol amide (CMEA) | | 0.85 | | 0.85 | | | |

-continued

| Ingredient | SH Ex 3 | SH Ex 4 | SH Ex 5 | SH Ex 6 | SH Ex 7 | SH Ex 8 | SH Ex 9 |
|---|---|---|---|---|---|---|---|
| Cetyl alcohol | | | 1 | | | | |
| Stearyl alcohol | | | 2 | | | | |
| MG1 Aptamer | 0.1 | 0.01 | 0.001 | 0.1 | 0.01 | .001 | .01 |
| Dimethicone | 1 | 1 | 1 | 1 | 1 | | 0.5 |
| Ethylene glycol distearate (EGDS) | 1.5 | 1.5 | 1.5 | 1.5 | 1.5 | | |
| Jaguar ® C5001 | 0.25 | 0.25 | 0.15 | | | | |
| Synthetic Cationic Polymer AMT2 | | | | 0.1 | | | |
| Polydiallyldimethylammonium chloride (DADMAC) | | | | | 0.1 | | |
| Excel Guar3 | | | | | | 0.1 | .15 |
| pH | 6 | 6 | 6 | 6 | 6 | 6 | |
| Water-USP Purified & Minors | Q.S. to 100 | Q.S. to 100 | Q.S. to 100 | Q.S. to 100 | Q.S. to 100 | Q.S. to 100 | Q.S. to 100 |

1 Cationic polymer derived from a natural gum with low aqueous viscosity
2 Cationic synthetic copolymer
3 Cationic plant derived polymer Rinse-Off Conditioner Formulations

| Ingredients | Rinse-off Conditioner Ex 1 Wt % | Rinse-off Conditioner Ex 2 Wt % |
|---|---|---|
| Amodimethicone 10000 cps | 0.50 | 0.50 |
| Citric acid anhydrous | 0.13 | 0.13 |
| DL-Panthenol 56% solution | 0.054 | 0.054 |
| Panthenyl Ethyl ether | 0.03 | 0.03 |
| Perfume | 0.50 | 0.50 |
| Hydroxypropyl guar (Jaguar HP-105) | 0.350 | 0.350 |
| Quaternium-18 | 0.750 | 0.750 |
| Steramidopropyldimethylamine | 1.00 | 1.00 |
| Gryceryl stearate | 0.25 | 0.25 |
| Cetearyl alcohol and Polysorbate 60 Emulsion 1 | 0.50 | 0.50 |
| Cetyl alcohol | 1.20 | 1.20 |
| Stearyl alcohol | 0.80 | 0.80 |
| Benzyl alcohol | 0.40 | 0.40 |
| Methylchloroisothiazolinone/ methylisothiazolinone | 0.033 | 0.033 |
| MG1 Aptamer | 0.01 | 0.001 |
| Water Purified | QS to 100 | QS to 100 |

1. Lipowax P from Lipo (looked in internet)

Additional Examples of Rinse-Off Hair Conditioning Compositions

| Components | Rinse-off Condition Ex. 3 | Rinse-off Condition Ex. 4 | Rinse-off Condition Ex. 5 | Rinse-off Condition Ex. 6 | Rinse-off Condition Ex. 7 | Rinse-off Condition Ex. 8 |
|---|---|---|---|---|---|---|
| Water-USP Purified & Minors | QS to 100% | QS to 100% | QS to 100% | QS to 100% | QS to 100% | QS to 100% |
| BTMS 1 | 2.3 | 2.3 | 2.3 | 2.3 | 2.3 | 2.3 |
| BTMAC 2 | — | — | — | — | — | — |
| Cetyl alcohol | 1.1 | 1.1 | 1.1 | 1.1 | 1.1 | 1.1 |
| Stearyl alcohol | 2.8 | 2.8 | 2.8 | 2.8 | 2.8 | 2.8 |
| Soy Oligomer 3 | 1.0 | — | | | — | — |
| Soy Oligomer Blend 4 | — | 1.0 | — | 1.0 | | |
| Aminosilicone 5 | 1.0 | 1.0 | 1.0 | | 2.0 | 2.0 |
| Perfume | 0.5 | 0.5 | 0.5 | 0.5 | 0.5 | 0.5 |
| Disodium EDTA | 0.1 | 0.1 | 0.1 | 0.1 | 0.1 | 0.1 |
| Panthenol | 0.03 | 0.03 | 0.03 | 0.03 | 0.03 | 0.03 |
| Panthenyl ethyl ether | 0.03 | 0.03 | 0.03 | 0.03 | 0.03 | 0.03 |
| MG1 Aptamer | 0.1 | 0.001 | 0.01 | 0.1 | 0.001 | .01 |
| Benzyl Alcohol | 0.4 | 0.4 | 0.4 | 0.4 | 0.4 | 0.4 |
| Preservatives | 0.03 | 0.03 | 0.03 | 0.03 | 0.03 | 0.03 |

| Ingredients | Rinse-off Condition Ex. 9 | Rinse-off Condition Ex. 10 | Rinse-off Condition Ex. 11 | Rinse-off Condition Ex. 12 | Rinse-off Condition Ex. 13 | Rinse-off Condition Ex. 14 |
|---|---|---|---|---|---|---|
| Water-USP Purified & Minors | QS to 100% | QS to 100% | QS to 100% | QS to 100% | QS to 100% | QS to 100% |
| BTMS1 | — | — | — | — | — | — |
| BTMAC2 | 2.8 | 2.8 | 2.8 | 2.8 | 2.8 | 2.8 |
| Cetyl alcohol | 1.8 | 1.8 | 1.8 | 1.8 | 1.8 | 1.8 |
| Stearyl alcohol | 4.6 | 4.6 | 4.6 | 4.6 | 4.6 | 4.6 |
| Soy Oligomer 3 | — | — | 0.75 | — | — | — |
| Soy Oligomer Blend 4 | — | 1.0 | — | | | |
| Aminosilicone 5 | 1.0 | — | 0.75 | 1.5 | 2.0 | 2.0 |

| | | | | | | |
|---|---|---|---|---|---|---|
| Perfume | 0.5 | 0.5 | 0.5 | 0.5 | 0.5 | 0.5 |
| Disodium EDTA | 0.1 | 0.1 | 0.1 | 0.1 | 0.1 | 0.1 |
| Panthenol | 0.03 | 0.03 | 0.03 | 0.03 | 0.03 | 0.03 |
| Panthenyl ethyl ether | 0.03 | 0.03 | 0.03 | 0.03 | 0.03 | 0.03 |
| MG1 Aptamer | 0.01 | 0.1 | 0.001 | 0.1 | 0.01 | 0.001 |
| Benzyl Alcohol | 0.4 | 0.4 | 0.4 | 0.4 | 0.4 | 0.4 |
| Preservatives | 0.03 | 0.03 | 0.03 | 0.03 | 0.03 | 0.03 |

| Ingredients | Rinse-off Condition Ex. 15 | Rinse-off Condition Ex. 16 | Rinse-off Condition Ex. 17 | Rinse-off Condition Ex. 18 |
|---|---|---|---|---|
| Water-USP Purified & Minors | QS to 100% | QS to 100% | QS to 100% | QS to 100% |
| BTMS 1 | 3.76 | 3.76 | 3.76 | 3.76 |
| BTMAC 2 | — | — | — | — |
| Cetyl alcohol | 1.3 | 1.3 | 1.3 | 1.3 |
| Stearyl alcohol | 3.2 | 3.2 | 3.2 | 3.2 |
| Soy Oligomer 3 | 1.0 | 1.0 | — | — |
| Soy Oligomer Blend 4 | — | — | — | — |
| Aminosilicone 5 | — | — | 1.0 | 1.0 |
| Perfume | 0.5 | 0.5 | 0.5 | 0.5 |
| Disodium EDTA | 0.1 | 0.1 | 0.1 | 0.1 |
| Panthenol | — | — | — | — |
| Panthenyl ethyl ether | — | — | — | — |
| MG1 Aptamer | 0.01 | 0.001 | 0.1 | 0.01 |
| Benzyl Alcohol | 0.4 | 0.4 | 0.4 | 0.4 |
| Preservatives | 0.03 | 0.03 | 0.03 | 0.03 |
| Deposition Aid polymer 6 | 0.5 | — | 0.5 | — |

1 Behenyltrimethylammonium methylsulfate, from Feixiang
2 Behenyltrimethylammonium chloride, Genamin KDMP, from Clariant
3 HY-3050, from Dow Corning
4 HY-3051, from Dow Corning
5 Y-14945; 10,000 cps aminodimethicone, from Momentive
6 ABC1459 from Mitsubishi Chemical Examples of Leave-on Treatment (Lot) Compositions

| Components | LOT Ex. 1 | LOT Ex. 2 | LOT Ex. 3 |
|---|---|---|---|
| Dipropyleneglycol Monomethylether | 0.500 | 0.500 | 0.500 |
| Disodium Ethylene diamine diacetic acid | 0.141 | 0.141 | 0.141 |
| PEG-40 Hydrogenated Castor Oil | 0.500 | 0.500 | 0.500 |
| Polysorbate 801 | 0.120 | 0.120 | — |
| Amodimethicone and Cetrimonium Chloride | 1.810 | 1.810 | 1.928 |
| Polyquaternium 112 | 1.335 | 1.335 | 1.335 |
| Citric Acid Anhydrous | 0.080 | 0.080 | 0.20 |
| 2-Amino-2-methyl-1-propanol | 0.100 | 0.100 | 0.100 |
| DMDM Hydantoin (55%)3 | 0.370 | — | — |
| Benzyl Alcohol | — | 0.400 | 0.4 |
| Neolone 950 Preservative4 | — | 0.053 | 0.053 |
| Perfume | 0.200 | 0.200 | 0.10 |
| MG1 Aptamer | 0.01 | 0.001 | 0.1 |
| Water-USP Purified & Minors | QS to 100% | QS to 100% | QS to 100% |

1Nonionic surfactant and emulsifier derived frompolyethoxylated sorbitan and oleic acid
2Copolymer of vinylpyrrolidone and quaternized dimethylaminoethyl methacrylate
31,3-Bis(hydroxymethyl)-5,5-dimethylimidazolidine-2,4-dione
4Preservative containing Methylisothiazolinone

V. Examples

Example 1. Aptamers Design

A. Growth of Fungus
A.1. Growth Conditions

*Malassezia globosa* ATCC® MYA-4612 are grown as a cell suspension in 50 mL of Modified Dixon Broth at 30-35° C. with constant shaking (250-300 rpm) in 250 mL autoclaved glass flasks. The broth is prepared by mixing the following materials: 36 g Bacto malt extract (VWR, catalog #90001-014), 20 g Difco Oxgall dehydrated fresh bile (VWR, catalog #90000-728), 10 mL tween 40 (Sigma, catalog #P1504), 36 g BBL polypeptone (BD, catalog #211677), 2 mL oleic acid (Sigma, catalog #01383), 2 mL glycerol (Sigma, catalog #G5516), and 1 L distilled water. The broth is autoclaved prior to use. After autoclaving, 0.5 mg of chloramphenicol (Sigma, catalog #C0378) is added.

A.2. Initial Inoculum

Cultures are initiated following ATCC recommendations. In summary, frozen ampoules are placed in a 25° C. water bath. Immediately after thawing, the surface of the ampoule is sterilized with 70% ethanol and the contents are aseptically transferred into an aliquot of the broth. An aliquot of the cultures is transferred to fresh broth every two weeks.

B. Aptamer Selection

B.1. Preparation of the Immobilization Field for FRELEX

An immobilization field is prepared by synthesizing a random library of eight nucleotide oligonucleotides with a disulfide group on the 5'-end (immobilization field library) (IDT DNA). The library is dissolved at a concentration of 10 μM in 1×PBS buffer. The surface of a gold coated glass slide with dimensions of 7 mm×10 mm×0.3 mm is used. This surface is treated with five sequential 10 μL drops of the immobilization field library. The slide is then allowed to incubate for 1 hour in the dark and in the presence of humidity in order to facilitate conjugation of the immobilization field library onto the gold surface.

After this incubation period, the immobilization field library is considered to have been conjugated onto the gold surface. The remaining solution is removed, and the surface is allowed to dry at room temperature.

The remaining surface is then blocked with short PEG molecules having the following general structure: CH3O—

(CH2CH2O)n-CH2CH2SH and an average molecular weight of 550 daltons. The PEG molecules are applied at a concentration of 286 µM in 1×PBS buffer and allowed to incubate overnight prior to removal. This process is repeated in a second blocking step with an incubation period of 30 minutes at room temperature.

Following blocking the chip is washed in 1×HEPES buffer (10 mM HEPES, pH 7.4, 120 mM NaCl, 5 mM KCl, 5 mM MgCl2) for 5 minutes with shaking at room temperature.

B.2. Library Preparation

A DNA library of about 1015 different sequences (10 nmoles), containing a random region of 40 nucleotides flanked by two conserved regions, i.e. a 5' forward primer recognition sequence (5'-TAGGGAAGAGAAGGACATAT-GAT-3') and a 3' reverse primer recognition sequence (5'-TTGACTAGTACATGACCACTTGA-3'), is solubilized in 100 µL of H2O and split into aliquots of 16.6 µL (about 1.66 nmoles of DNA). An equimolar amount of blockers that bind the primer regions sequences (5'-AT-CATATGTCCTTCTCTTCCCTA-3' and 5'-TCAAGTGGT-CATGTACTAGTCAA-3'), selection buffer (final concentration: 10 mM HEPES; pH 7.3), and water are incubated with the selection library in a total volume of 50 µL. The library solution with the blockers is denatured for 5 minutes at 95° C. to heat-denature the DNA. After this step, the temperature is decreased by one degree per minute to allow the blockers to anneal. When needed, 5 µL of a commercial antidandruff shampoo with zinc pyrithione is substituted for water in the 50 µL library solution.

B.3. Negative Selection with FRELEX

Aptamer selection is performed in two sequential steps. In the first step (negative selection), the library is enriched for aptamers that did not bind to shampoo formulation components using the FRELEX protocol. In the second step (positive selection), the library is enriched for sequences that bound to *Malassezia globosa* ATCC® MYA-4612.

FRELEX is an aptamer selection platform (Lecocq S. et al., "Aptamers as biomarkers for neurological disorders. Proof of concept in transgenic mice" Plos One 19326201, Jan. 5, 2018, Vol. 13, Issue 1) that enables partitioning of aptamers into bound and unbound states. During the negative selection, this approach is only used to select aptamer sequences that did not bind to undesirable target molecules.

First, the immobilization field described in section B.1. is placed inside a Petri dish. An aliquot of 50 µl of selection library solution (prepared as described in section B.2.) is added slowly to the top surface of the gold chip and incubated for 30 minutes at room temperature with gentle shaking (50 rpm). The supernatant solution is then removed from the immobilization field and discarded. It is presumed that the removed DNA sequences are either those that had too much secondary structure to facilitate hybridization to the immobilized 8-mers or those that are bound to compounds that are present in the negative selection library. Starting in selection round 2 and continuing for all subsequent selection rounds, 5 µL of a commercial antidandruff shampoo with zinc pyrithione is substituted for water in the 50 µL selection library solution. Thus, aptamers that bound to any compound within this formulation are discarded.

The immobilization field is then washed twice with 50 µL of 10×TE buffer (pH 7.3) and each wash solution is also discarded. Finally, the chip is placed inside a 2 mL plastic tube in the presence of 0.6 mL of selection buffer and heated to 95° C. for 15 minutes to denature the hybridized aptamers from the 8-mers and to release them into the solution. The solution is transferred to a fresh 1.5 mL Eppendorf tube. The recovered aptamer library is purified with a Genejet PCR cleanup kit (ThermoFisher Scientific, Catalog #K0702) according to manufacturer's instructions.

B.4. Positive Selection

During each selection round, negative selection as described in section B.3. is applied first. Then, the aptamers remaining from this process are used for positive selection. The completion of a negative selection process and a positive selection process constituted a single selection round.

For each positive selection, between $1.5 \times 10^5$ and $3.0 \times 10^6$ cells are collected from the broth suspension. The required broth volume is determined by counting cells in a defined volume with a Haemacytometer. The cells are pelleted gently (800 g) to remove the growth broth and washed twice with 1 mL of selection buffer followed by gentle centrifugation. The DNA library from the negative selection (described in section B.3.) is applied to the pellet (total volume of 250 µL). Then, the cells are resuspended and incubated with the aptamer library for 30 minutes at 35° C. with gentle rotation, followed by centrifugation (800 g) and removal of the supernatant. With this step, aptamers that did not bind to the fungal cells are discarded. Finally, the cell pellet is washed twice with 500 µL of selection buffer by pipetting the solution up and down and the cells are recovered by gentle centrifugation (800 g).

Aptamers bound to the cells are then recovered by resuspending the pellet in 500 µL of lysis solution (1 N NaOH) followed by incubation for 10 minutes at 95° C. with gently mixing. The suspension is pelleted again by centrifugation and the supernatant containing the bound aptamers are recovered. The pellet is resuspended one more time in 500 µL of lysis buffer, incubated, and centrifuged, and the supernatant is recovered. The two separate aliquots of recovered aptamers are combined and purified using a GeneJET PCR Purification Kit (ThermoFisher Scientific, Catalog # K0702), following manufacturer's instructions.

The recovered library is PCR amplified in two stages. First, the purified library is subjected to test PCR reactions using several aliquots of 5 µL of recovered library and increasing number cycles. The products of these test PCR reactions are analyzed by polyacrylamide electrophoresis and the optimum number of cycles is determined. Then, a larger portion of the recovered library is amplified using this number of cycles. PCR amplification is carried out with Taq buffer (5 µL; New England BioLabs, Catalog #B9014S), Taq DNA polymerase (0.25 µL; New England BioLabs, Catalog # M0273X), dNTPs mixture solution (10 mM each, 1 µL; New England BioLabs, Catalog #N0447L), forward primer (10 µM, 1 µL), reverse primer (10 µM, 1 µL), water (36.75 µL) and library template (5 µL). PCR reactions are performed with an annealing temperature of 55° C. for the first two selection rounds and an annealing temperature of 60° C. for subsequent selection rounds.

C. Aptamers Sequencing

After 8 selection rounds, the aptamer libraries are sequenced. In summary, the selected libraries 3 to 8 are prepared for next generation sequencing (NGS) through a two-step PCR process. In the first step, a different hex code (6 base sequence) and a portion of a universal sequencing primer is added to the 5' end of each aptamer library. In the second step, complete universal sequencing primers are added to both ends. After the second PCR step, the libraries are purified through acrylamide electrophoresis and balanced for relative quantity. These libraries are then pooled and sent to the Hospital for Sick Children in Toronto for NGS with an Illumina HiSeq 2500 instrument.

The sequencing data is tabulated and analyzed. A total of 25,895,781 sequences are analyzed and each library contained more than 300,000 sequences (see FIG. 1). The sequences from selection round 8 are sorted by copy number and named in descending order with the highest copy number sequence being named Mg-1. These top sequences are listed in Table 1.

The copy numbers of the top sequences of selection round 8 (Table 1) are determined on the libraries obtained from the other selection rounds. Finally, the frequency is computed for each sequence by dividing observed copy number by the total number of sequences observed in the particular library. Enrichment trajectories of the top 20 sequences in terms of frequency across different selection rounds are plotted (see FIG. 2). During the selection, these sequences are enriching at a similar rate.

Example 2. Aptamers Binding

Quantitative polymerase chain reaction (qPCR) is used to determine the amount of aptamer bound to the target. In brief, a 5 µL aliquot of the eluted aptamer and an aliquot of SYBR green are mixed and the DNA is PCR amplified. As the concentration of double stranded DNA increases, the fluorescent signal also increases, providing an indication on the relative amounts of eluted aptamer (see FIG. 3). The results indicate that aptamers Mg-1 and Mg-2 bound to the fungal cells significantly better than aptamer Mg-4.

The Ct value is the number of PCR cycles at which the sample crosses a threshold detection value. In the FIG. 4, the Ct values are adjusted for the amplification efficiency for each of the aptamers. The selected aptamers have significant secondary structure and thus amplify less efficiently than the negative sequence.

Example 3. Motif Analysis

The frequency of motifs of six nucleotides from the random regions of the top two aptamers (Mg-1 and Mg-2) within all the sequences of selection round 8 library is determined. Then, the average motif frequency is subtracted from the frequency of each motif and this value is divided by the standard deviation of all the motifs frequencies in that selection round, resulting in a Z value for every motif (see FIGS. 5 and 7). It stands to reason that sequences containing high frequency motifs also bind to *M. globosa* may be part of the present invention.

The prediction of the secondary structures of the aptamers is performed with DINAmelt (http://unafold.rna.albany.edu/?q=DINAMelt/Quickfold; from RNA Institute of College of Arts and Sciences of the State University of New York at Albany) and the motifs are highlighted within these structures (see FIGS. 6 and 8).

A. Analysis of random region of aptamer Mg-1:
The motifs:

```
SEQ ID NO 101:
5'-GGTATGAAG-3'

SEQ ID NO 102:
5'-AAAATG-3'

SEQ ID NO 103:
5'-GGTATGAAGNNNNNNNANNAAAATG-3'
``` from the variable region of sequence Mg-1 (SEQ ID NO 1):

```
5'-TTGAGACGGTATGAAGGCTTTTGAGAAAATGCGCCACGAA-3'
``` where N stands for any nucleotide, are found at a significantly higher frequency than would be expected randomly. This means that these particular motifs are positively selected for within this *M. globosa* based aptamer selection process. Any sequences containing this motif are also expected to bind to *M. globosa* may be part of the present invention.

B. Analysis of random region of aptamer Mg-2:
The analysis of the variable region of Mg-2 (SEQ ID NO 2):

```
5'-TGGCAAGTATTTGTACATATACTGACGTTTGCCTTACTGC-3'
``` suggests that the entire sequence has been selected for.

Example 4. Analysis of Sequences Similarity

Alignment of SEQ ID NO 1 to SEQ ID NO 100 is performed using the software Align X, a component of Vector NTI Advanced 11.5.4 by Invitrogen. Several groups of sequences have at least 90%, at least 70%, or at least 50% nucleotide sequence identity as illustrated in the alignments of FIGS. 9, 10, and 11. In these alignments, only the central variable region of the aptamers is included for simplicity. Thus, oligonucleotides with at least 50%, at least 70%, or at least 90% nucleotide sequence identity to sequences selected from the group consisting of SEQ ID NO 1 to SEQ ID NO 100 are included and may be part of the current invention.

Example 5. Delivery of Personal Care Active Ingredients with Aptamers

Aptamers of the current invention are chemically synthesized. A solution of a personal care active ingredient containing a free amine group (0.25 M) and imidazole (0.1 M) in water (pH 6) is prepared. Then, EDC (1-ethyl-3-[3-dimethylaminopropyl]carbodiimide hydrochloride) is weighed in a reaction vial and mixed with an aliquot of an aptamer solution. An aliquot of the amine/imidazole solution is added immediately to the reaction vial and vortexed until all the components are dissolved. An additional aliquot of imidazole solution (0.1 M, pH 6) is added to the reaction vial and the reaction mixture is incubated at room temperature for at least 2 hours. Following incubation, the unreacted EDC and its by-products and imidazole are separated from the modified aptamer by dialysis or by using a spin desalting column and a suitable buffer (e.g. 10 mM sodium phosphate, 0.15 M NaCl, 10 mM EDTA, pH 7.2). Additional details about the conjugation protocols are described in Hermanson G. T., "Bioconjugate Techniques", pp. 969-1002, 2nd Edition, Academic Press, San Diego, 2008, the content of which is incorporated herein by reference.

The produced modified aptamer conjugated with a personal care active ingredient can be formulated in a hair care composition (e.g. shampoo or conditioner) to provide benefits when contacted with hair.

TABLE 1

List of top sequences from selection experiment.

| SEQ ID NO | Name | Sequence |
|---|---|---|
| 1 | Mg-1 | TAGGGAAGAGAAGGACATATGATTTGAGACGGTATGAAGGCTTTTGAGAAAATGCGCCACGAATTGACTAGTACATGACCACTTGA |
| 2 | Mg-2 | TAGGGAAGAGAAGGACATATGATTGGCAAGTATTTGTACATATACTGACGTTTGCCTTACTGCTTGACTAGTACATGACCACTTGA |
| 3 | Mg-3 | TAGGGAAGAGAAGGACATATGATGACCGAGGTTCCGGCGACAGAGCAAATTTGTAATTTGGAGTTGACTAGTACATGACCACTTGA |
| 4 | Mg-4 | TAGGGAAGAGAAGGACATATGATCACGAAACATAAGTTGTGTCAGAATACACCTGTTTCCCTGTTGACTAGTACATGACCACTTGA |
| 5 | Mg-5 | TAGGGAAGAGAAGGACATATGATTAAAGAACAGGATGATCAGGGTTGATGGATTTTGACGATGTTGACTAGTACATGACCACTTGA |
| 6 | Mg-6 | TAGGGAAGAGAAGGACATATGATTCCTCTGCTGGTGAGAGGCGTCCAATGAATCATATTACCGTTGACTAGTACATGACCACTTGA |
| 7 | Mg-7 | TAGGGAAGAGAAGGACATATGATAGTCAAATAAAATTTTGTGTGAATCGAGTGTGCTATTGCTTTGACTAGTACATGACCACTTGA |
| 8 | Mg-8 | TAGGGAAGAGAAGGACATATGATGGTGTTGAAAGTTATGTAATTATTTAGGGAACGTATGGACTTGACTAGTACATGACCACTTGA |
| 9 | Mg-9 | TAGGGAAGAGAAGGACATATGATGGGGAAGAGTGATAATCTAAAGGTACTACAATGTACTACATTGACTAGTACATGACCACTTGA |
| 10 | Mg-10 | TAGGGAAGAGAAGGACATATGATTAGCAAGTATTTGTACATATACTGACGTTTGCCTTACTGCTTGACTAGTACATGACCACTTGA |
| 11 | Mg-11 | TAGGGAAGAGAAGGACATATGATACCCTCGATACGTATATTCGATATGAGGGAGTATTCCGTGTTGACTAGTACATGACCACTTGA |
| 12 | Mg-12 | TAGGGAAGAGAAGGACATATGATGAGTAACAGTTCAACCTTGTTATTACACTAACTCCGTGACTTGACTAGTACATGACCACTTGA |
| 13 | Mg-13 | TAGGGAAGAGAAGGACATATGATGATGTTGATAAATTTGCAATGACTAGATCCATCCGCTTTATTGACTAGTACATGACCACTTGA |
| 14 | Mg-14 | TAGGGAAGAGAAGGACATATGATGAACGGATCCGATACGAACGTTAACAAATGAGGGTTTAAGTTGACTAGTACATGACCACTTGA |
| 15 | Mg-15 | TAGGGAAGAGAAGGACATATGATAATTGATATGCAGCAATTACCAGTATAAGGCATCTACTACTTGACTAGTACATGACCACTTGA |
| 16 | Mg-16 | TAGGGAAGAGAAGGACATATGATCCATTTTCTCGACTTTGCCATTGCTATAAATAGCTTCACATTGACTAGTACATGACCACTTGA |
| 17 | Mg-17 | TAGGGAAGAGAAGGACATATGATTGGCAAATATTTGTACATATACTGACGTTTGCCTTACTGCTTGACTAGTACATGACCACTTGA |
| 18 | Mg-18 | TAGGGAAGAGAAGGACATATGATATATTCACGCTAGTGGGAGCGCTGTTGATCATACGGCTGCTTGACTAGTACATGACCACTTGA |
| 19 | Mg-19 | TAGGGAAGAGAAGGACATATGATTGGCAAGTATTTGTACATATACTGACGTTTGTCTTACTGCTTGACTAGTACATGACCACTTGA |
| 20 | Mg-20 | TAGGGAAGAGAAGGACATATGATCACGAAACATAAGTTGTGTCAGAATACACCTGTTTCTCTGTTGACTAGTACATGACCACTTGA |
| 21 | Mg-21 | TAGGGAAGAGAAGGACATATGATATTAAGTTAGGTCCGTAATGACACTTAAACGGATCCATACTTGACTAGTACATGACCACTTGA |
| 22 | Mg-22 | TAGGGAAGAGAAGGACATATGATTGGCAAGTATTTGTACATATACTGACGTTTGCCTTACTACTTGACTAGTACATGACCACTTGA |
| 23 | Mg-23 | TAGGGAAGAGAAGGACATATGATTAAAGAACAGGATGATCAGGGTTGATGGATTTTGATGATGTTGACTAGTACATGACCACTTGA |
| 24 | Mg-24 | TAGGGAAGAGAAGGACATATGATTAGGCTAACTGTTCAGGGATTTGATATGCATGAGGAGCACTTGACTAGTACATGACCACTTGA |
| 25 | Mg-25 | TAGGGAAGAGAAGGACATATGATTGGCAAGTATTTGTACATATACTAACGTTTGCCTTACTGCTTGACTAGTACATGACCACTTGA |
| 26 | Mg-26 | TAGGGAAGAGAAGGACATATGATTGACAAGTATTTGTACATATACTGACGTTTGCCTTACTGCTTGACTAGTACATGACCACTTGA |
| 27 | Mg-27 | TAGGGAAGAGAAGGACATATGATTCTCGAGTGCAAAAACGTTGAGCCAAGAATTTAACCTATCTTGACTAGTACATGACCACTTGA |
| 28 | Mg-28 | TAGGGAAGAGAAGGACATATGATTGGCAAGTATTTGTACATATACTGACGTTTGCCTTACTGTTTGACTAGTACATGACCACTTGA |
| 29 | Mg-29 | TAGGGAAGAGAAGGACATATGATTGGCAAGTATTTGTACATATACTGATGTTTGCCTTACTGCTTGACTAGTACATGACCACTTGA |
| 30 | Mg-30 | TAGGGAAGAGAAGGACATATGATTGGCAAGTATTTGTACATATACTGACGTTTGCCTTATTGCTTGACTAGTACATGACCACTTGA |
| 31 | Mg-31 | TAGGGAAGAGAAGGACATATGATTGGTAAGTATTTGTACATATACTGACGTTTGCCTTACTGCTTGACTAGTACATGACCACTTGA |
| 32 | Mg-32 | TAGGGAAGAGAAGGACATATGATGTCAATCTATCACAAACGCGAGGTAAGGCCCACGCGATTATTGACTAGTACATGACCACTTGA |
| 33 | Mg-33 | TAGGGAAGAGAAGGACATATGATCGCTCTAATTGGCGTGGAGGGAGTGTTCCTCCAACGGTAATTGACTAGTACATGACCACTTGA |
| 34 | Mg-34 | TAGGGAAGAGAAGGACATATGATGCATGCACGTCTGAAGAAATCCTTGAATTGTACCGGAAGATTGACTAGTACATGACCACTTGA |
| 35 | Mg-35 | TAGGGAAGAGAAGGACATATGATTGGCAAGTATTTGTACATATACTGACGTTTACCTTACTGCTTGACTAGTACATGACCACTTGA |
| 36 | Mg-36 | TAGGGAAGAGAAGGACATATGATCTAAACAGTACTTCAACCTAAAGAGTCACGTACGCAGTAATTGACTAGTACATGACCACTTGA |

TABLE 1-continued

List of top sequences from selection experiment.

| SEQ ID NO | Name | Sequence |
|---|---|---|
| 37 | Mg-37 | TAGGGAAGAGAAGGACATATGATTGCCATCGTATAAATCTCAAAAGGGATCATTGTAAAATCCTTGACTAGTACATGACCACTTGA |
| 38 | Mg-38 | TAGGGAAGAGAAGGACATATGATCTGGGGGCTTCCCGGAGTTCCGTAAAGTAGTGAGATCTTGTTGACTAGTACATGACCACTTGA |
| 39 | Mg-39 | TAGGGAAGAGAAGGACATATGATTTGTGATCAAGAAAATGGAACCCACATAACTATTCCGAGTTTGACTAGTACATGACCACTTGA |
| 40 | Mg-40 | TAGGGAAGAGAAGGACATATGATGAGCCTAGATCATTTTGATCTTGCAATCTATGGCAGAATCTTGACTAGTACATGACCACTTGA |
| 41 | Mg-41 | TAGGGAAGAGAAGGACATATGATACAATTTGGATAGTACCGCGATCAGGTACAAAGAATATTCTTGACTAGTACATGACCACTTGA |
| 42 | Mg-42 | TAGGGAAGAGAAGGACATATGATGCATTCACAGTAGCAATTGTATTTCCTTGATAGGAATGAATTGACTAGTACATGACCACTTGA |
| 43 | Mg-43 | TAGGGAAGAGAAGGACATATGATCACGAAACATAAGTTGTGTCAGAATACACCTATTTCCCTGTTGACTAGTACATGACCACTTGA |
| 44 | Mg-44 | TAGGGAAGAGAAGGACATATGATTGGCAAGTATTTGTACATATATTGACGTTTGCCTTACTGCTTGACTAGTACATGACCACTTGA |
| 45 | Mg-45 | TAGGGAAGAGAAGGACATATGATTGTGAAACCAAATAGAAGATATAACACTCTTATCTACAGTTGACTAGTACATGACCACTTGA |
| 46 | Mg-46 | TAGGGAAGAGAAGGACATATGATTGAAGTGGAGACCGTAGAGGGAGATTACAATATGAATCCGGTTGACTAGTACATGACCACTTGA |
| 47 | Mg-47 | TAGGGAAGAGAAGGACATATGATTGGCAAGTATTTGTACATATACTGACATTTGCCTTACTGCTTGACTAGTACATGACCACTTGA |
| 48 | Mg-48 | TAGGGAAGAGAAGGACATATGATCTCAGTACTGCAAGGATTTAAGATACAGCGCATTGCAGAATTGACTAGTACATGACCACTTGA |
| 49 | Mg-49 | TAGGGAAGAGAAGGACATATGATTGGCAAGTATTTATACATATACTGACGTTTGCCTTACTGCTTGACTAGTACATGACCACTTGA |
| 50 | Mg-50 | TAGGGAAGAGAAGGACATATGATTTAAACAGGATCCGCACGAATACAGTGTACACAATTCAGGTTGACTAGTACATGACCACTTGA |
| 51 | Mg-51 | TAGGGAAGAGAAGGACATATGATCTATGGATCGACTAGTAATCAAGCCTTCGGACTCTTATGATTGACTAGTACATGACCACTTGA |
| 52 | Mg-52 | TAGGGAAGAGAAGGACATATGATTGGGACGTAACAGTATGAACTTGAAGACTTATCATTGTATTGACTAGTACATGACCACTTGA |
| 53 | Mg-53 | TAGGGAAGAGAAGGACATATGATTGGCAAGTATTTGTATATATACTGACGTTTGCCTTACTGCTTGACTAGTACATGACCACTTGA |
| 54 | Mg-54 | TAGGGAAGAGAAGGACATATGATTGGCAAGTATTTGTACATATACTGACGTTTGCTTTACTGCTTGACTAGTACATGACCACTTGA |
| 55 | Mg-55 | TAGGGAAGAGAAGGACATATGATCAGGAATGCTTCAATTCCTTGTAGCATTCACTTGTAGACATTGACTAGTACATGACCACTTGA |
| 56 | Mg-56 | TAGGGAAGAGAAGGACATATGATTACGGGGATAAGGAGCAACATATTAAGCAAAGTACTAAAATTGACTAGTACATGACCACTTGA |
| 57 | Mg-57 | TAGGGAAGAGAAGGACATATGATAAAACATGAAGCTGAACGCGTAACTCCCGGCTGGCGAATATTGACTAGTACATGACCACTTGA |
| 58 | Mg-58 | TAGGGAAGAGAAGGACATATGATCACGAAACATAAGTTGTGTCAGAATATACCTGTTTCCCTGTTGACTAGTACATGACCACTTGA |
| 59 | Mg-59 | TAGGGAAGAGAAGGACATATGATCTGACGGGAGTCAGAACCCTTGTTAAGGGACCACCTGTTTTTGACTAGTACATGACCACTTGA |
| 60 | Mg-60 | TAGGGAAGAGAAGGACATATGATGTAAGACTTGTACTATGAAATGTTATGGAGGATGTAGATTTTGACTAGTACATGACCACTTGA |
| 61 | Mg-61 | TAGGGAAGAGAAGGACATATGATGCCGTAAGAAACCTCCTGGTGTTCGAAATATGGAAAGTCTTTGACTAGTACATGACCACTTGA |
| 62 | Mg-62 | TAGGGAAGAGAAGGACATATGATGAGTTTTAAAAGGCAATATGTCTTGAGAGACAAGGTTAGATTGACTAGTACATGACCACTTGA |
| 63 | Mg-63 | TAGGGAAGAGAAGGACATATGATATTGACATTCTAAGCTAATGAAAGTGTAATAACGACTAGCTTGACTAGTACATGACCACTTGA |
| 64 | Mg-64 | TAGGGAAGAGAAGGACATATGATCACGAAACATAAGTTGTGTCAGAATACACCTGTTTCCCTATTGACTAGTACATGACCACTTGA |
| 65 | Mg-65 | TAGGGAAGAGAAGGACATATGATCACGAAACATAAGTTATGTCAGAATACACCTGTTTCCCTGTTGACTAGTACATGACCACTTGA |
| 66 | Mg-66 | TAGGGAAGAGAAGGACATATGATTCCTCTGCTGGTGAGAGGTGTCCAATGAATCATATTACCGTTGACTAGTACATGACCACTTGA |
| 67 | Mg-67 | TAGGGAAGAGAAGGACATATGATAGAGTAAGAATCCATAATTTGGCAAGTAGACATTCGCATATTGACTAGTACATGACCACTTGA |
| 68 | Mg-68 | TAGGGAAGAGAAGGACATATGATGTTTAGGACGTATCTTAGAGCTGGCCCTCAATGAAAGGTTTTGACTAGTACATGACCACTTGA |
| 69 | Mg-69 | TAGGGAAGAGAAGGACATATGATGAGAGGCAGTAGGTCTAATGAAGAATCTCTAGGTTGCAAATTGACTAGTACATGACCACTTGA |
| 70 | Mg-70 | TAGGGAAGAGAAGGACATATGATGGCCTATACTTGGTTGCTTCTATAGCTTAGTGCGGGGATTTGACTAGTACATGACCACTTGA |
| 71 | Mg-71 | TAGGGAAGAGAAGGACATATGATCACGAAACATAAGTTGTGTCAGAATACACTTGTTTCCCTGTTGACTAGTACATGACCACTTGA |
| 72 | Mg-72 | TAGGGAAGAGAAGGACATATGATCACGAAACATAAATTGTGTCAGAATACACCTGTTTCCCTGTTGACTAGTACATGACCACTTGA |

TABLE 1-continued

List of top sequences from selection experiment.

| SEQ ID NO | Name | Sequence |
|---|---|---|
| 73 | Mg-73 | TAGGGAAGAGAAGGACATATGATCTGACGGGAGTCAGAACCCTTGTTAAGGGATCACCTGTTTTTGACTAGTACATGACCACTTGA |
| 74 | Mg-74 | TAGGGAAGAGAAGGACATATGATTCCTCTGTTGGTGAGAGGCGTCCAATGAATCATATTACCGTTGACTAGTACATGACCACTTGA |
| 75 | Mg-75 | TAGGGAAGAGAAGGACATATGATCACAACGTAATTTTCGGGTGAATGATGCAGCCAAGAGAAATTGACTAGTACATGACCACTTGA |
| 76 | Mg-76 | TAGGGAAGAGAAGGACATATGATTAAGTTGGAAAGTGGTAGAATGCTTAGACAGGCGGGGGACTTGACTAGTACATGACCACTTGA |
| 77 | Mg-77 | TAGGGAAGAGAAGGACATATGATGTTATAATGGTGCAAACTATAGCTAATAAGATGCCACTGATTGACTAGTACATGACCACTTGA |
| 78 | Mg-78 | TAGGGAAGAGAAGGACATATGATGTGAATTCGCATGACTTGGAAGAGGTAAACAAAAGTAGCTTTGACTAGTACATGACCACTTGA |
| 79 | Mg-79 | TAGGGAAGAGAAGGACATATGATAAGGTTTACTCAACTCGGATTCAAAGAACATGTACTTAACTTGACTAGTACATGACCACTTGA |
| 80 | Mg-80 | TAGGGAAGAGAAGGACATATGATCACGAAACATAAGTTGTGTCAGAATACATCTGTTTCCCTGTTGACTAGTACATGACCACTTGA |
| 81 | Mg-81 | TAGGGAAGAGAAGGACATATGATGCTCGTTTATTCGGACCTCAGGGGCTGTCAGCATTTGAATTTGACTAGTACATGACCACTTGA |
| 82 | Mg-82 | TAGGGAAGAGAAGGACATATGATTGCGGCTATAAGTTTATGTGTGAATATTGGTATGATATAATTGACTAGTACATGACCACTTGA |
| 83 | Mg-83 | TAGGGAAGAGAAGGACATATGATGACGCACAGTATGCGTGCTATCAATTTTGAGTATAGTGTATTGACTAGTACATGACCACTTGA |
| 84 | Mg-84 | TAGGGAAGAGAAGGACATATGATTGGCAAGTATTTGTACATATACTGACGCTTGCCTTACTGCTTGACTAGTACATGACCACTTGA |
| 85 | Mg-85 | TAGGGAAGAGAAGGACATATGATTCCTCTGCTGGTGAGAGGCGTTCAATGAATCATATTACCGTTGACTAGTACATGACCACTTGA |
| 86 | Mg-86 | TAGGGAAGAGAAGGACATATGATTCCTTTGCTGGTGAGAGGCGTCCAATGAATCATATTACCGTTGACTAGTACATGACCACTTGA |
| 87 | Mg-87 | TAGGGAAGAGAAGGACATATGATCTGACACCATTTTACAAATTGAAATAATACAGCTTATACGTTGACTAGTACATGACCACTTGA |
| 88 | Mg-88 | TAGGGAAGAGAAGGACATATGATCCGCCTGACGAACACAAGGAACCGGAATTAAGCGAATGCCTTGACTAGTACATGACCACTTGA |
| 89 | Mg-89 | TAGGGAAGAGAAGGACATATGATTGACTAGTACATGACCACTTGAGATCGGAAGAGCACACGTTTGACTAGTACATGACCACTTGA |
| 90 | Mg-90 | TAGGGAAGAGAAGGACATATGATCTTATACCAATCAATAACGCGCATTTTTAGCAAGACAAGATTGACTAGTACATGACCACTTGA |
| 91 | Mg-91 | TAGGGAAGAGAAGGACATATGATTAAAGAACAAGATGATCAGGGTTGATGGATTTTGACGATGTTGACTAGTACATGACCACTTGA |
| 92 | Mg-92 | TAGGGAAGAGAAGGACATATGATTAAAGAATAGGATGATCAGGGTTGATGGATTTTGACGATGTTGACTAGTACATGACCACTTGA |
| 93 | Mg-93 | TAGGGAAGAGAAGGACATATGATTCGCAGAATTCTAATAGACCTGGAGAAGACAGGGGGTTATTTGACTAGTACATGACCACTTGA |
| 94 | Mg-94 | TAGGGAAGAGAAGGACATATGATATTACGAGTTTATAAGATTTGGCGCTGCCTACTCATCATCTTGACTAGTACATGACCACTTGA |
| 95 | Mg-95 | TAGGGAAGAGAAGGACATATGATTAAAGAACAAGATAATCAGGGTTGATGGATTTTGACGATGTTGACTAGTACATGACCACTTGA |
| 96 | Mg-96 | TAGGGAAGAGAAGGACATATGATACATAAAATTTCCAGATCTACCTGATGTGTGCCGTCTATATTGACTAGTACATGACCACTTGA |
| 97 | Mg-97 | TAGGGAAGAGAAGGACATATGATCGGATGAATAAACAATGCTGGGTACTGATCAGTATGACCTTTGACTAGTACATGACCACTTGA |
| 98 | Mg-98 | TAGGGAAGAGAAGGACATATGATGAAGGGCAAGCCTTATAAATTCGTACTGTATCTTATTGAATTGACTAGTACATGACCACTTGA |
| 99 | Mg-99 | TAGGGAAGAGAAGGACATATGATCGGTGTCGGTAGAAACAAAGAGAGGTTATGCATATCTATGTTGACTAGTACATGACCACTTGA |
| 100 | Mg-100 | TAGGGAAGAGAAGGACATATGATCAAGGATGTCATGGAACTGGTGAACTGTCTAAAATCACCATTGACTAGTACATGACCACTTGA |

Additional Combinations/Examples

A. An aptamer composition comprising at least one oligonucleotide consisting of: deoxyribonucleotides, ribonucleotides, derivatives of deoxyribonucleotides, derivatives of ribonucleotides, and mixtures thereof; wherein said aptamer composition has a binding affinity for one or more fungi species from the genus *Malassezia*.

B. The aptamer composition according to Paragraph A, wherein said one or more fungi species are selected from the group consisting of: *M. globosa, M. furfur, M. restricta, M. caprae, M. cuniculi, M. dermatis, M. equine, M. japonica, M. nana, M. obtuse, M. pachydermatis, M. slooffiae, M. sympodialis, M. yamatoensis*, and mixtures thereof.

C. The aptamer composition according to Paragraph A-B, wherein said one or more fungi species are selected from the group consisting of: *M. globosa, M. furfur, M. restricta*, and mixtures thereof.

D. The aptamer composition according to Paragraph A-C, comprising at least one oligonucleotide selected from the group consisting of oligonucleotides with at least 50% nucleotide sequence identity to sequences selected from the group consisting of SEQ ID NO 1 to SEQ ID NO 100.

E. The aptamer composition according to Paragraph A-D, comprising at least one oligonucleotide selected from the group consisting of SEQ ID NO 1 to SEQ ID NO 100.
F. The aptamer composition according to Paragraph A-E, comprising at least one oligonucleotide selected from the group consisting of SEQ ID NO 1, SEQ ID NO 2, and SEQ ID NO 4.
G. The aptamer composition according to Paragraph A-F, wherein said at least one oligonucleotide comprises one or more motifs selected from the group consisting of SEQ ID NO 101, SEQ ID NO 102, and SEQ ID NO 103.
H. The aptamer composition according to Paragraph A-G, wherein said at least one oligonucleotide comprises natural or non-natural nucleobases.
I. The aptamer composition according to Paragraph A-H, wherein said non-natural nucleobases are selected from the group comprising hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, and mixtures thereof.
J. The aptamer composition according to Paragraph A-I, wherein the nucleosides of said at least one oligonucleotide are linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, and mixtures thereof.
K. The aptamer composition according to Paragraph A-J, where said derivatives of ribonucleotides or said derivatives of deoxyribonucleotides are selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.
L. The aptamer composition according to Paragraph A-K, further comprising at least one polymeric material, wherein said at least one polymeric material is covalently linked to said at least one oligonucleotide.
M. The aptamer composition according to Paragraph A-L, wherein said at least one polymeric material is polyethylene glycol.
N. The aptamer composition according to Paragraph A-M, wherein the nucleotides at the 5'- and 3'-ends of said at least one oligonucleotide are inverted.
O. The aptamer composition according to Paragraph A-N, wherein at least one nucleotide of said at least one oligonucleotide is fluorinated at the 2' position of the pentose group.
P. The aptamer composition according to Paragraph A-0, wherein the pyrimidine nucleotides of said at least one oligonucleotide are fluorinated at the 2' position of the pentose group.
Q. The aptamer composition according to Paragraph A-P, wherein said at least one oligonucleotide is covalently or non-covalently attached to one or more personal care benefit agents, wherein said one or more personal care benefit agents are selected from the group comprising: anti-fungal agents, cooling agents, natural extracts, peptides, enzymes, conditioning agents, scalp health agents, anti-frizz agents, gloss improving agents, hair strengthening agents, hair growth actives, artificial color preserving agents, perfumes, malodor absorbing agents, styling agents, chelants, hair coloring dyes, sebum absorbing agents, sebum modification agents, and mixtures thereof.
R. The aptamer composition according to Paragraph A-Q, wherein said one or more personal care active ingredients are selected from the group consisting of anti-fungal agents.
S. The aptamer composition according to Paragraph A-R, wherein said one or more personal care active ingredients are selected from the group consisting of zinc pyrithione, piroctone olamine, ketoconazole, and selenium disulfide.
T. The aptamer composition according to Paragraph A-R, wherein said at least one oligonucleotide is covalently or non-covalently attached to one or more nanomaterials.
U. A personal care composition according to Paragraph A-T, comprising at least one nucleic acid aptamer; wherein said at least one nucleic acid aptamer has a binding affinity for one or more fungi species from the genus *Malassezia*.
V. The personal care composition according to Paragraph A-U, wherein said one or more fungi species are selected from the group consisting of: *M. globosa, M. furfur, M. restricta, M. caprae, M. cuniculi, M. dermatis, M. equine, M. japonica, M. nana, M. obtuse, M. pachydermatis, M. slooffiae, M. sympodialis, M. yamatoensis*, and mixtures thereof.
W. The personal care composition according to Paragraph A-U, wherein said one or more fungi species are selected from the group consisting of: *M. globosa, M. furfur, M. restricta*, and mixtures thereof.
X. The personal care composition according to Paragraph A-W, wherein said composition comprises at least two different nucleic acid aptamers; and wherein said at least two different nucleic acid aptamers have binding affinities for different epitopes of said one or more fungi species from the genus *Malassezia*.
Y. A method for delivering one or more personal care active ingredients to the scalp or the skin according to Paragraph A-X, comprising administering a personal care composition comprising at least one nucleic acid aptamer and one or more personal care active ingredients; wherein said at least one nucleic acid aptamer and said one or more personal care active ingredients are covalently or non-covalently attached; and wherein said at least one nucleic acid aptamer has a binding affinity for one or more fungi species from the genus *Malassezia*.
Z. The method according to Paragraph A-Y, wherein said one or more fungi species are selected from the group consisting of: *M. globosa, M. furfur, M. restricta*, and mixtures thereof.
AA. The method according to Paragraph A-Z, where said one or more personal care active ingredients are selected from the group comprising antifungal agents.

BB. A method for delivering one or more personal care active ingredients to the scalp or the skin according to Paragraph A-AA, comprising administering a personal care composition comprising: at least one nucleic acid aptamer and one or more nanomaterials; wherein said at least one nucleic acid aptamer and said one or more nanomaterials are covalently or non-covalently attached; wherein said at least one nucleic acid aptamer has a binding affinity for one or more fungi species from the genus *Malassezia*; and wherein said one or more nanomaterials comprise one or more personal care active ingredients.

CC. A diagnostic method for detecting a fungus on a surface or a liquid according to Paragraph A-BB wherein said diagnostic method comprises:
  a. mixing the liquid with, or contacting the surface a diagnostic composition comprising:
    (1) an aptamer composition comprising at least one oligonucleotide consisting of deoxyribonucleotides, ribonucleotides, derivatives of deoxyribonucleotides, derivatives of ribonucleotides, and mixtures thereof; wherein said aptamer composition has a binding affinity for one or more fungi species
    (2) a detection agent composition which enables the detection of the complex of the fungi species and the aptamer;
  b. Detecting the presence of the complex of the fungi species and the aptamer.

DD. The diagnostic method according to Paragraph A-CC, wherein the surface is scalp, skin, foot, other body parts, surfaces of articles which come into contact with human hands or other parts of human body or pet body and cause contamination.

EE. The diagnostic method according to Paragraph A-DD, wherein the liquid is blood, other body fluids, intravenous drugs, other drugs, food sources, food preparation, drinking water, or other water supply.

FF. The diagnostic method according to Paragraph A-EE, wherein the fungus is *malassezia*.

GG. The diagnostic method according to Paragraph A-FF, wherein the contacting of the diagnostic composition with surface is performed by rubbing (a) a swab or (b) a woven substrate or (c) or nonwoven substrate or (d) comb, which comprise a region having an absorbing element comprising the aptamer composition and a detection agent composition.

HH. The diagnostic method according to Paragraph A-GG, wherein the detecting step is observed by a color change developed by the creation of the complex of the fungi species and the aptamer composition in the presence of the detection agent composition.

II. The diagnostic method according to Paragraph A-HH, wherein the detecting step comprises an analytical determination using x ray, other spectroscopic techniques, MRI, radionuclide techniques which can quantitatively determine the creation of the complex of the fungi species and the aptamer composition in the presence of the detection agent composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While the present invention has been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aptamer composition comprising at least one oligonucleotide consisting of: deoxyribonucleotides, ribonucleotides, derivatives of deoxyribonucleotides, derivatives of ribonucleotides, and mixtures thereof; wherein said aptamer composition has a binding affinity for one or more fungi species from the genus *Malassezia* wherein at least one oligonucleotide is selected from the group consisting of SEQ ID NO: 1 to SEQ ID NO: 100.

2. The aptamer composition of claim 1, wherein said at least one oligonucleotide comprises one or more motifs selected from the group consisting of SEQ ID NO 101, SEQ ID NO 102, and SEQ ID NO 103.

3. The aptamer composition of claim 1, wherein said at least one oligonucleotide comprises non-natural nucleobases.

4. The aptamer composition of claim 3, wherein said non-natural nucleobases are selected from the group comprising hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, and mixtures thereof.

5. The aptamer composition of claim 1, wherein the nucleosides of said at least one oligonucleotide are linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, and mixtures thereof.

6. The aptamer composition of claim 1, where said derivatives of ribonucleotides or said derivatives of deoxyribonucleotides are selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

7. The aptamer composition of claim 1, further comprising at least one polymeric material, wherein said at least one polymeric material is covalently linked to said at least one oligonucleotide.

8. The aptamer composition of claim 1, wherein said at least one polymeric material is polyethylene glycol.

9. The aptamer composition of claim 1, wherein the nucleotides at the 5'- and 3'-ends of said at least one oligonucleotide are inverted.

10. The aptamer composition of claim 1, wherein at least one nucleotide of said at least one oligonucleotide is fluorinated at the 2' position of the pentose group.

11. The aptamer composition of claim 1, wherein the pyrimidine nucleotides of said at least one oligonucleotide are fluorinated at the 2' position of the pentose group.

12. The aptamer composition of claim 1, wherein said at least one oligonucleotide is covalently or non-covalently attached to one or more personal care benefit agents, wherein said one or more personal care benefit agents are selected from the group comprising: anti-fungal agents, cooling agents, natural extracts, peptides, enzymes, conditioning agents, scalp health agents, anti-frizz agents, gloss improving agents, hair strengthening agents, hair growth actives, artificial color preserving agents, perfumes, malodor absorbing agents, styling agents, chelants, hair coloring dyes, sebum absorbing agents, sebum modification agents, and mixtures thereof.

13. The aptamer composition of claim 12, wherein said one or more personal care active ingredients are selected from the group consisting of antifungal agents.

14. The aptamer composition of claim 13, wherein said one or more personal care active ingredients are selected from the group consisting of zinc pyrithione, piroctone olamine, ketoconazole, and selenium disulfide.

15. The aptamer composition of claim 1, wherein said at least one oligonucleotide is covalently or non-covalently attached to one or more nanomaterials.

16. A personal care composition comprising at least one nucleic acid aptamer; comprising at least one oligonucleotide consisting of: deoxyribonucleotides, ribonucleotides, derivatives of deoxyribonucleotides, derivatives of ribonucleotides, and mixtures thereof; wherein said at least one nucleic acid aptamer has a binding affinity for one or more fungi species from the genus *Malassezia* wherein at least one oligonucleotide is selected from the group consisting of SEQ ID NO: 1 to SEQ ID NO: 100 and comprising one or more personal care active ingredients.

17. The personal care composition of claim 16, wherein said composition comprises at least two different nucleic acid aptamers; and wherein said at least two different nucleic acid aptamers have binding affinities for different epitopes of said one or more fungi species from the genus *Malassezia*.

18. An aptamer composition comprising at least one oligonucleotide consisting of: deoxyribonucleotides, ribonucleotides, derivatives of deoxyribonucleotides, derivatives of ribonucleotides, and mixtures thereof; wherein said aptamer composition has a binding affinity for one or more fungi species from the genus *Malassezia* comprising at least one oligonucleotide is selected from the group consisting of SEQ ID NO 1 to SEQ ID NO 10.

\* \* \* \* \*